(12) United States Patent
Belide et al.

(10) Patent No.: US 11,917,960 B2
(45) Date of Patent: Mar. 5, 2024

(54) METHODS TO IMPROVE GENETIC TRANSFORMATION OF SORGHUM

(71) Applicant: Commonwealth Scientific and Industrial Research Organisation, Acton (AU)

(72) Inventors: Srinivas Belide, Moncrieff (AU); James Robertson Petrie, Goulburn (AU); Surinder Pal Singh, Downer (AU)

(73) Assignee: COMMONWEALTH SCIENTIFIC AND INDUSTRIAL RESEARCH ORGANISATION, Acton (AU)

( * ) Notice: Subject to any disclaimer, the term of this patent is extended or adjusted under 35 U.S.C. 154(b) by 0 days.

(21) Appl. No.: 16/308,577

(22) PCT Filed: May 17, 2017

(86) PCT No.: PCT/AU2017/050459
§ 371 (c)(1),
(2) Date: Dec. 10, 2018

(87) PCT Pub. No.: WO2017/210719
PCT Pub. Date: Dec. 14, 2017

(65) Prior Publication Data
US 2020/0315115 A1    Oct. 8, 2020

(30) Foreign Application Priority Data
Jun. 10, 2016  (AU) ............................. 2016902278

(51) Int. Cl.
*C12N 15/82* (2006.01)
*A01H 4/00* (2006.01)

(52) U.S. Cl.
CPC .................................... *A01H 4/005* (2013.01)

(58) Field of Classification Search
None
See application file for complete search history.

(56) References Cited

U.S. PATENT DOCUMENTS

| | | | |
|---|---|---|---|
| 6,686,513 B1 | 2/2004 | Albert et al. | |
| 8,404,930 B2 | 3/2013 | Wu | |
| 8,431,402 B2 * | 4/2013 | Vasudevan | ............... A01G 2/00 435/430.1 |
| 2004/0133938 A1 * | 7/2004 | Dan | ..................... C12N 5/0025 800/278 |
| 2006/0212970 A1 * | 9/2006 | Bhat | .................. C12N 15/8216 800/287 |

FOREIGN PATENT DOCUMENTS

| | | |
|---|---|---|
| WO | WO 2010/011175 A1 | 1/2010 |
| WO | WO 2010/094421 A1 | 8/2011 |

OTHER PUBLICATIONS

Liu and Godwin. Plant Cell Rep (2012) 31:999-1007.*
Wu et al. In Vitro Cell.Dev.Biol. Plant (2014)50:9-18.*
Zhao et al. African Journal of Biotechnology (2010), vol. 9(16), pp. 2367-2374.*
Zhao et al. Plant Mol. Biol (2000), Vo. 44:789-798.*
Packer et al. Free Radicle Biology and Medicine (1995), vol. 19(2):227-250.*
International Search Report and Written Opinion of the International Searching Authority dated Aug. 10, 2017 in connection with PCT International Application No. PCT/AU2017/050459.
Belide, S. et al., "Robust genetic transformation of sorghum (*Sorghum bicolor*) using green regenerative tissue:", In Vitro Cellular & Developmental Biology—Animal, 2016, vol. 52, Suppl. 1, pp. S55-S56.
Dan, Y., et al. "Liopic acid—an unique plant transformation enhancer." In Vitro Cellular & Developmental Biology—Plant, 2009, vol. 45, pp. 630-638.
Dora, S.V.V.N. et al., "Efficient callus induction protocol for *Sorghum bicolor*", Asian Journal of Plant Science and Research, 2014, vol. 4, pp. 14-21.
Sant, R.R.P. Development of a transformation system for sorghum (*Sorghum bicolor* L. ) 2011 (Doctoral dissertation, Queensland University of Technology), abstract.
Sudhakar, P. et al. "Plant tissue culture studies in Sorghum bicolor; immature embryo explants as the source material" International Journal of Plant Production, 2008, vol. 2, pp. 1-14.
Apr. 30, 2020 Response dated Oct. 22, 2019 Communication Pursuant to Rules 70 (2) and 70a (2) EPC filed in connection with European Patent Application No. 17809438.9.
Feb. 11, 2020 European Examination Report issued in connection with corresponding European patent application No. 17809438.9.
May 12, 2021 Response to European Examination Report filed in connection with corresponding European patent application No. 17809438.9.
Able, J.A., et al. "The Investigation of Optimal Bombardment Parameters for Transient and Stable TransgeneExpression in Sorghum", In Vitro Cellular & Developmental Biology. Plant, 37;3: 341-348 (May-Jun. 2001).
Belide, S., et al. "Robust genetic transformation of sorghum (*Sorghum bicolor* L.) using differentiating embryogenic callus induced from immature embryos", Plant Methods, 13;109: 1-12 (2017).
Casas, A.M., et al. "Transgenic sorghum plants via microprojectile bombardment", Proc. Nat'l. Acad. Sci. USA, 90: 11212-11216 (Dec. 1993).

(Continued)

*Primary Examiner* — Medina A Ibrahim
(74) *Attorney, Agent, or Firm* — Gary J. Gershik

(57) ABSTRACT

The invention provides an improved method for transformation of sorghum and the production of genetically modified sorghum. In particular, methods and means are described for the production of high quality, transformable sorghum plant cells which are maintained in culture for longer duration without losing their regenerative potential and their use for genetic transformation. The method also describes the use of improved media for efficient plant regeneration from transformed plant cells, thereby providing significant improvement in the stable transformation frequency of sorghum.

7 Claims, 7 Drawing Sheets
Specification includes a Sequence Listing.

(56) References Cited

OTHER PUBLICATIONS

Cho, M.-J., et al. "Stable transformation of rice (*Oryza sativa* L.) via microprojectile bombardment of highly regenerative, green tissues derived from mature seed", Plant Cell Rep., 22: 483-489 (2004).

Cho, M.-J., et al. "Agrobacterium-mediated high-frequency transformation of an elite commercial maize (*Zea mays* L.) inbred line", Plant Cell Rep., 33: 1767-1777 (2014).

Howe, A., et al. "Rapid and reproducible Agrobacterium-mediated transformation of sorghum", Plant Cell Rep., 25: 784-791 (2006).

Ishida, Y., et al. "High efficiency transformation of maize (*Zea mays* L.) mediated by Agrobacterium tumefaciens", Nature Biotechnology, 14: 745-750 (Jun. 14, 1996).

Dan, Y. "Biological functions of antioxidants in plan transformation", In Vitro Cell Dev. Biol.—Plant, 44: 149-161 (2008).

Li, J., et al. "Development of a simple and efficient method for Agrobacterium—Mediated Transformation in Sorghum", Int. J. Agric. Biol., 18: 134-138 (2016).

Liu, G., et al. "A robust tissue culture system for sorghum [*Sorghum bicolor* (L.) Moench]", South African Journal of Botany, 98: 157-160 (2015).

Tadesse, Y., et al. "Optimisation of transformation conditions and production of transgenic sorghum (*Sorghum bicolor*) via microparticle bombardment", Plant Cell, Tissue and Organ Culture, 75: 1-18 (2003).

Visarada, K.B.R.S., and Sai Kishore, N. "Advances in Genetic Transformation", Sorghum Molecular Breeding (R. Madhusudhana et al eds.), Springer India: 199-215 (2015).

May 11, 2021 Office Action issued in connection with corresponding Japanese patent application No. 2018-564307, including English translation.

Pola, S., et al. "Plant tissue culture studies in Sorghum bicolor: immature embryo explants as the source material", International Journal of Plant Production, 2(1): 1-14 (Jan. 2008).

Prasad Sant, R.R. "Development of a transformation system for sorghum (*Sorghum bicolor* L.)", A thesis submitted for the degree of Doctor of Philosophy at the Queensland University of Technology, 2011, Chapter 3, 6, p. 26-50, 106-133.

Polumahanthi, S., et al. "Efficient callus induction protocol for Sorghum bicolor", Asian Journal of Plant Science and Research, 4(3): 14-21 (2014).

Nov. 2, 2020 Communication Pursuant to Article 94(3) EPC issued in connection with corresponding European patent application No. 17809438.9.

Apr. 12, 2022 English language summary of First Office Action issued in connection with Mexican Patent Application No. MX/a/2018/015234.

Jan. 31, 2022 Office Action issued in connection with corresponding Japanese Patent Application No. 2018-564307 including English language translation thereof.

May 20, 2022 First Office Action and Search Report issued in connection with Chinese Patent Application No. 201780042875.X including English language translation thereof.

\* cited by examiner

METHODS TO IMPROVE GENETIC TRANSFORMATION OF SORGHUM

CROSS-REFERENCE TO RELATED APPLICATIONS

This application is a § 371 national stage of PCT International Application No. PCT/AU2017/050459, filed May 17, 2017, claiming priority of Australian Patent Application No. 2016902278, filed Jun. 10, 2016, the contents of each of which are hereby incorporated by reference into the application.

REFERENCE TO A SEQUENCE LISTING

This application incorporates-by-reference nucleotide and/or amino acid sequences which are present in the file named "181210_5938_90762_Sequence_Listing_GJG.txt", which is 2 kilobytes in size, and which was created Dec. 5, 2018 in the IBM-PC machine format, having an operating system compatibility with MS-Windows, which is contained in the text file filed Dec. 10, 2018 as part of this application.

RELATED APPLICATION DATA

The present application claims priority from Australian Provisional Application No. 2016902278 filed on 10 Jun. 2016, the full contents of which is incorporated herein by reference.

FIELD OF THE INVENTION

The present disclosure relates to methods of efficient plant regeneration and genetic transformation of sorghum.

BACKGROUND OF THE INVENTION

Sorghum is an important cereal crop grown for multiple uses such as food, forage, fodder and bioenergy. Sorghum is a versatile crop having an ability to grow in a wide range of temperatures and climatic conditions and is relatively tolerant to drought and soil toxicities relative to other cereal crops. Utilisation of, and interest in, sorghum grain as a foodstuff is on the increase as the market looks for suitable gluten-free alternative grains to cater for consumers suffering from gluten sensitivities e.g., such as with coeliac disease.

As more genes and regulatory elements are identified from sorghum, along with advances in metabolomics and genomics, the possibility of applying genetic engineering for beneficial production and utilisation of sorghum is also increasing (Venkatesh et al., 2015). Historically, however, sorghum has been considered a difficult crop for tissue culture and transformation (Grootboom et al., 2010), due to the factors such as accumulation of phenolic compounds in cell culture (Gurel et al., 2009), lack of model genotypes, low regeneration frequency and loss of regeneration potential through sub-cultures (Visarada and Kishore, 2015). A highly efficient and comprehensive transformation system therefore remains elusive for sorghum (Liu et al., 2015), thereby limiting the potential for genetic engineering of this important crop.

Particle bombardment and *Agrobacterium*-mediated transformation are the two main approaches that have been utilized to produce transgenic plants, including sorghum. The first successful genetic transformation of sorghum was reported by Casas et al. (1993) using particle bombardment with immature embryos as the plant tissue, to achieve a transformation frequency of 0.08% transformants per bombarded embryo. Several modifications to this method have since been reported, including optimization of tissue culture conditions and other parameters (Able et al., 2001; Tadesee et al., 2003; Masheswari et al., 2010), resulting in transformation efficiencies in the range of 1-7% per embryo. Liu and Godwin (2012) reported further significant improvement over the previously published methods by using immature embryos of sorghum variety TX430 and optimized media composition. The first successful report of *Agrobacterium*-mediated transformation of sorghum was by Zhao et al. (2000).

Since this first report, a number of modified and improved protocols for *Agrobacterium*-mediated transformation of sorghum have published, including reports by Howe et al. (2006) and Shridhar et al. (2010), where transformation frequencies of 4.5% and 4.28% per embryo, respectively, were achieved. More recently, Wu et al. (2014) reported improvements in *Agrobacterium*-mediated transformation frequency of sorghum using immature embryos with superbinary vectors (Ishida et al., 1996) and modified culture media. However, since optimisation of tissue culture methods appears to have plateaued, researchers have now turned to alternative approaches for the transformation of sorghum which do not rely on tissue culture e.g., as described in Li et al. (2016). Even with these extensive optimisation efforts and improved transformation reports, sorghum still lags behind other cereals in terms of transformation frequency and is still considered to be a recalcitrant and difficult plant to transform. Visarada and Kishore (2015) reviewed this area and concluded that, for sorghum, cell transformation followed by regeneration remains extremely complicated.

Among different tissue explants used for successful genetic transformation of sorghum by either particle bombardment or *Agrobacterium* methods, immature embryos are the choice of explants relative to mature seed-derived explants (e.g. shoot tip) and all of the more efficient transformation protocols reported to date have used immature embryos (Liu et al., 2012 and 2014; Wu et al., 2014). Zhao et al. (2000) has also shown statistically that the source of the embryos has a very significant impact on sorghum transformation efficiency.

There is a need for further methods for transforming sorghum plants with improve efficiency, as well as further tissue explants and culture mediums which may be used to achieve improved transformation efficiency in sorghum.

SUMMARY OF THE INVENTION

The present invention is based, in part, on recognition by the inventors that differentiating embryogenic callus (DEC) tissue induced from isolated immature embryos from sorghum may provide a flexible choice of explant for transformation of sorghum, which is independent of environmental factors, and which may be used to improve transformation efficiency.

Thus, in one example, the present disclosure provides method for preparing differentiating embryogenic callus (DEC) tissue of sorghum, comprising culturing isolated immature embryos (IEs) from sorghum in callus inducing medium (CIM) for a time and under conditions sufficient to produce DEC tissue from the IEs, wherein the CIM comprises a basal medium suitable for culturing plant cells supplemented with one or more auxins, one or more cytokinins and one or more agents which reduces oxidative browning.

In one example, the IEs are derived from a cultivar of *Sorghum bicolor*. For example, the IEs may be derived from a sweet sorghum cultivar of *Sorghum bicolor*. For example, the IEs may be derived from a grain sorghum cultivar of. In one example, the IEs may be derived from a sorghum line selected from the group consisting of IEsCS3541, M91051, SRN39, Shanqui red, IS8260, IS4225, Tx430, P898012, P954035 and PP290. In one example, the IEs may be derived from the sorghum line designated Tx430. In one example, the IEs may be derived from the sorghum line designated IEsCS3541. In one example, the IEs may be derived from the sorghum line designated M91051. In one example, the IEs may be derived from the sorghum line designated SRN39. In one example, the IEs may be derived from the sorghum line designated Shanqui red. In one example, the IEs may be derived from the sorghum line designated IS8260. In. one example, the IEs may be derived from the sorghum line designated IS4225. In one example, the IEs may be derived from the sorghum line designated P898012. In one example, the IEs may be derived from the sorghum line designated P954035. In one example, the IEs may be derived from the sorghum line designated PP290.

In one example, the CIM comprises one or more agents which reduces oxidative browning selected from the group consisting of lipoic acid, melatonin, 2-aminoidan-2-phosphonic acid, ascorbic acid, alpha-tocopherol, 3,5-dibutyl-4-hydroxytoluene (BHT), cysteine, selenite, polyvinylpolypyrrolidone (PVPP), dithiothreitol (DTT), phenoxane, silver nitrate, citrate, glutathione, phytic acid, nordihydroguaiaretic acid (NDGA), and activated charcoal.

In one example, the one or more agents which reduces oxidative browning are present in the CIM at a concentration of about 0.1 mg/L to about 5 mg/L, about 0.5 g/L to about 5 g/L, about 1 g/L to about 5 g/L, or about 1 g/L.

In one example, the CIM comprises one or more auxins selected from the group consisting of indole-3-acetic acid (IAA), 4-chloroindole-3-acetic acid, phenylacetic acid, indole-3-butyric acid (IBA), 1-naphthaleneacetic acid (NAA), 2-naphthoxyacetic acid, 4-chlorophenoxyacetic acid, 2,4-dichlorophenoxyacetic acid (2,4-D), 2,4,5-Trichlorophenoxyacetic acid, 2,3,5-Triiodobenzoic acid, picloram, and salt forms of any one thereof.

In one example, the one or more auxins are present in the CIM at a concentration of about 0.1 mg/L to about 5 mg/L, about 0.1 mg/L to about 3 mg/L, about 0.3 mg/L to about 2 mg/L, or about 0.5 mg/L to about 1 mg/L.

In one example, the one or more cytokinins are selected from the group consisting of benzylaminopurine (BAP), zeatin, kinetin, 2IP, zeatin riboside, diphenylurea and thidiazuron (TDZ).

In one example, the one or more cytokinins are present in the CIM at a concentration of about 0.01 mg/L to about 2 mg/L, about 0.1 mg/L to about 2 mg/L, about 0.5 mg/L to about 2 mg/L, about 0.5 mg/L to about 1 mg/L, or about 0.5 mg/L.

In one example, the one or more auxins and the one or more cytokinins are present in the CIM in amounts relative to one another which is sufficient to produce and/or maintain the DECs from the IEs.

In one example, the one or more auxins and the one or more cytokinins are present in the CIM at a weight ratio (auxin:cytokinin) of about 1.25:1, about 1.5:1, about 1.75:1, about 2:1, about 2.25:1, about 2.5:1, about 2.75:1, or about 3:1.

In one preferred example, CIM comprises lipoic acid e.g., α-lipoic acid. In a particularly preferred example, the CIM comprises lipoic acid at a concentration of about 0.5 mg/L to about 2.0 mg/L, or about 1 mg/L. For example, CIM comprises lipoic acid at concentration of about 1 mg/L.

In one example, the CIM comprises peptone. For example, the CIM may comprise peptone at a concentration of about 0.2 g/L to about 2 g/L, about 0.5 g/L to about 1.5 g/L, about 0.7 g/L to about 1 g/L, or about 0.8 g/L. In one example, the CIM comprises lipoic acid e.g., α-lipoic acid, at concentration of about 1 mg/L.

In one example, the CIM comprises copper. For example, when copper is present it may be provided in the form of cupric sulfate, copper chloride, copper nitrate, copper gluconate, or copper acetate. For example, when copper is present, the copper is present at a concentration of about 0.1 mg/L to about 5 mg/L, about 0.3 mg/L to about 3 mg/L, about 0.5 mg/L to about 1.5 mg/L, about 0.7 mg/L to about 1 mg/L, or about 0.8 mg/L. In one example, the copper is provided in the form of copper sulfate at concentration of about 0.8 mg/L.

In one example, the CIM comprises an osmotic agent.

In one example, the method comprises culturing the IEs under dim light conditions for a time sufficient to produce the DEC tissue. For example, the culturing of the IEs may occur under dim light conditions having a light intensity of about 10 µmol s$^{-1}$ m$^{-2}$ to about 55 µmol s$^{-1}$ m$^{-2}$, or about 30 µmol s$^{-1}$ m$^{-2}$ to about 50 µmol s$^{-1}$ m$^{-2}$, or about 45 mol s$^{-1}$ m$^{-2}$ to about 50 µmol s$^{-1}$ m$^{-2}$.

Preferably the light is white light i.e., light emitted at wavelength(s) corresponding to the white light spectrum.

In one example, the method comprises wherein culturing the IEs with a photoperiod of about 12 h to about 20 h, about 14 h to about 18 h, or about 16 h. Preferably, the photoperiod is 16 h.

In one example, the time sufficient to produce the DEC tissue is at least about 2 to about 6 weeks, about 3 to about 5 weeks, or about 4 weeks.

In one example, the method comprises at least one subculturing step comprising transferring DEC tissue to fresh CIM and culturing the DEC tissue in the fresh CIM.

According to an example comprising at least one subculturing step, the at least one subculturing step comprises culturing the transferred DEC tissue in fresh CIM under substantially the same conditions used to produce the DEC tissue.

In one example, the method comprises repeating the subculture step every 2 to 4 weeks to maintain the DEC tissue.

In one example, the method comprises repeating the subculture step in order to maintain the DEC tissue for at least 4 months, at least 5 months, at least 6 months, at least 7 months, at least 8 months and/or up to 12 months from the time that the DEC tissue was produced from the IEs.

In another example, the method results in an at least 60%, or at least 65%, or at least 70%, or at least 75%, callus induction frequency from immature embryos.

The present disclosure also provides a method of producing a genetically modified sorghum cell, said method comprising introducing one or more nucleic acids into differentiating embryogenic callus (DEC) tissue of sorghum.

In an example, the method has an average transformation frequency of at least 40% or at least 45%, or about 40% to about 50%. The transformation frequency means the number of regenerated transformed plants per DEC tissue, expressed as a percentage.

The present disclosure also provides a method of producing a genetically-modified sorghum plant or regenerative part thereof, said method comprising in order:

(a) producing a genetically modified sorghum cell, preferably a grain sorghum cell, by introducing one or more nucleic acids into differentiating embryogenic callus (DEC) tissue of sorghum;
(b) culturing the DEC tissue(s) into which the one or more nucleic acids have been introduced on a medium, or a series of media, such that said culturing induces shoot formation from the DEC tissue(s), thereby producing one or more genetically modified shoot;
(c) producing one or more genetically modified sorghum plants from the genetically modified shoot of step (b), thereby producing the genetically-modified sorghum plant(s); and optionally
(d) obtaining regenerative parts from the genetically modified plant(s) of step (c).

The present disclosure also provides a method of producing a genetically-modified sorghum plant or regenerative part thereof, preferably a grain sorghum plant or part thereof, said method comprising in order:
(a) introducing one or more nucleic acids into a population of sorghum tissues;
(b) culturing the sorghum tissues into which the one or more nucleic acids have been introduced on a medium, or a series of media, such that said culturing induces shoot formation from said sorghum tissues at an efficiency of at least 35 genetically modified shoots per 100 sorghum tissues into which the one or more nucleic acids has been introduced, thereby producing genetically modified shoots; and
(c) producing one or more genetically modified sorghum plants from the genetically-modified shoots of step (b), thereby producing the genetically modified sorghum plant(s); and optionally
(d) obtaining a regenerative part from the genetically modified plant(s) of step (c).

In one example of the method of producing a genetically modified sorghum cell, at least one of the one or more nucleic acids comprises a selectable marker gene, and step (b) comprises selecting for tissue(s) into which the selectable marker gene has been introduced.

In one example, the one or more nucleic acids are introduced into the sorghum tissue(s) by bacteria-mediated transformation, microprojectile-mediated transformation, electroporation, microinjection, polyethylene glycol (PEG)-induced fusion or liposome-mediate transfer.

In one example, the bacteria used in the bacteria-mediated transformation is selected from the group consisting of *Agrobacterium* sp., *Rhizobium* sp., *Sinorhizobium meliloti, Mezorhizobium loti, Escherichia coli, Shigella flexneri, Salmonella typhimurium, Listeria monocytogenes, Yersinia pseudotuberculosis*, and *Yersinia enterocolitica*.

In one example, the nucleic acid is introduced into the DEC tissue by *Agrobacterium*-mediated transformation.

In one example, the nucleic acid is introduced into the DEC tissue by microprojectile-mediated transformation.

In one example, the nucleic acid comprises a polynucleotide encoding a selectable marker, and the one or more selection steps comprises selecting transformed DEC tissue based on detection of expression of the selectable marker.

In one example, the selectable marker is a fluorescent or bioluminescent marker which can be expressed by transformants, and the one or more selection steps comprises selecting for transformed DEC tissue or plant tissue grown therefrom expressing the fluorescent or bioluminescent marker.

In one example, the fluorescent or bioluminescent marker is selected from expressed forms of green fluorescent protein (GFP), blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz, GFPuv, destabilised EGFP (dEGFP), destabilised ECFP (dECFP), destabilised EYFP (dEYFP), HcRed, t-HcRed, DsRed, DsRed2, t-dimer2, t-dimer2(12), mRFP1, pocilloporin, *Renilla* GFP, Monster GFP, paGFP, Kaede protein, a Phycobiliprotein, a luciferase, or a biologically active variant or fragment of any one thereof.

In one example, one of the nucleic acid(s) comprises a polynucleotide encoding a selectable marker which confers antibiotic resistance to transformants, and the one or more selection steps comprises culturing the transformed DEC tissue or plant tissue grown therefrom in the presence of the corresponding antibiotic. For example, the polynucleotide encoding a selectable marker confers antibiotic resistance to hygromycin, glufosinate, kanamycin, or phosphinothricin.

In one example, the nucleic acid comprises a polynucleotide encoding a selectable marker which confers herbicide resistance to transformants, and the one or more selection steps comprises culturing the transformed DEC tissue or plant tissue grown therefrom in the presence of the corresponding herbicide. For example, the polynucleotide encoding a selectable marker confers herbicide resistance to glyphosate, glufosinate, or bialaphos.

In one example, the nucleic acid comprises a polynucleotide encoding a positive selectable marker which confers a selective advantage e.g., a growth advantage, to transformants in the presence of a metabolite, and the one or more selection steps comprises culturing the transformed DEC tissue or plant tissue grown therefrom in the presence of a corresponding metabolite of the positive selectable marker. For example, the polynucleotide encoding a selectable marker which confers a selective growth advantage to a transformant in the presence of a metabolite is a trehalase, β-glucoronidase (GUS) gene or phosphomannose isomerase (PMI) gene.

In one example, the medium, or at least one of the media in the series, used to culture the sorghum tissue(s) at step (b) comprises a CIM as defined herein.

In one example, the step (b) of the method of producing a genetically modified sorghum plant comprises culturing the sorghum tissue(s) on one or more of the media in the series under dim light conditions, followed by culturing the sorghum tissue(s) on one or more further media in the series under light conditions having a greater intensity than the dim light conditions.

In one example, the dim light conditions are characterised by a light intensity of about 10 µmol $s^{-1}$ $m^{-2}$ to about 55 µmol $s^{-1}$ $m^{-2}$, about 30 µmol $s^{-1}$ $m^{-2}$ to about 50 µmol $s^{-1}$ $m^{-2}$, or about 45 µmol $s^{-1}$ $m^{-2}$ to about 50 µmol $s^{-1}$ $m^{-2}$. In a preferred example, the dim light conditions comprise white light irradiated at an intensity of about 30 µmol $m^{-2}$ $sec^{-1}$ to about 45 µmol $m^{-2}$ $sec^{-1}$.

In one example, the light conditions having a greater intensity than the dim light conditions are characterised by a light intensity of about 55 µmol $s^{-1}$ $m^{-2}$ to about 90 µmol $s^{-1}$ $m^{-2}$, about 60 µmol $s^{-1}$ $m^{-2}$ to about 85 µmol $s^{-1}$ $m^{-2}$, or about 65 µmol $s^{-1}$ $m^{-2}$ to about 80 µmol $s^{-1}$ $m^{-2}$.

In accordance with an example in which the dim light conditions comprise white light irradiated at an intensity of about 30 µmol $m^{-2}$ $sec^{-1}$ to about 45 µmol $m^{-2}$ $sec^{-1}$, the culturing of the tissue(s) on the further media occurs under white light having an intensity of about 65 g mol $s^{-1}$ $m^{-2}$ to about 80 µmol $s^{-1}$ $m^{-2}$.

In one example, the culturing at step (b) of the method occurs with a photoperiod of about 12 h to about 20 h, about 14 h to about 18 h, or about 16 h. Preferably, the culturing at step (b) of the method occurs with a photoperiod of 16 h.

In one example, culturing the sorghum tissue(s) on the medium, or on each medium in the series of media, occurs, independently, for about 1 week, about 2 weeks, about 3 weeks, about 4 weeks, about 5 weeks, or about 6 weeks.

In one example, the method of producing a genetically modified sorghum plant further comprises splitting the sorghum tissue(s), each into two or more parts, after introduction of the one or more nucleic acids.

In one example, one or more of the series of media at step (b) of the method comprises L-cysteine and/or ascorbic acid. In one example, the CIM comprises L-cysteine and/or ascorbic acid.

Also provided is a method of producing a genetically modified sorghum plant, preferably a grain sorghum plant, in which a genetic modification efficiency of at least about 35%, at least about 40%, at least about 45%, at least about 50%, at least about 55%, at least about 60%, at least about 65%, at least about 70%, at least about 75%, at least about 80%, at least about 85%, or at least about 90% is obtained, wherein the genetic modification efficiency is expressed as the number of genetically modified shoots produced in step (b) as a percentage of the number of DEC tissues or sorghum tissues used in step (a). For example, the method of producing a genetically modified sorghum plant is the method as hereinbefore described.

In one example, the method of producing a genetically modified sorghum plant or a regenerative part thereof, further comprising:
(i) obtaining the DEC tissue(s) of sorghum;
(ii) obtaining DEC tissue(s) produced by the method of the disclosure; or
(iii) producing the DEC tissue(s) of sorghum by performing the method of the disclosure.

The present disclosure also provides a method of producing progeny of a genetically-modified sorghum plant, preferably a grain sorghum plant, the method comprising selfing or crossing a genetically modified sorghum plant produced using the method of the disclosure, to thereby produce progeny plants.

In one example, the method of producing progeny of a genetically-modified sorghum plant further comprises
(i) screening the progeny plants for the presence of the genetic modification or a phenotype conferred by the genetic modification; and
(ii) selecting progeny plants comprising the genetic modification and/or which display a phenotype conferred by the genetic modification, to thereby produce the one or more genetically modified sorghum plant(s).

The present disclosure also provides a genetically modified sorghum plant, progeny or part thereof produced using a method of the disclosure, preferably a grain sorghum plant, progeny or part thereof, wherein the sorghum plant, progeny or part thereof comprises a genetic modification introduced by the method. For example, the part thereof is an organ, tissue or cell of sorghum, comprising the genetic modification. In a preferred example, the plant part is selected from the group consisting of seed, leaf and stem.

The present disclosure also provides a culture medium suitable for use in preparing differentiating embryogenic callus (DEC) tissue of sorghum, said culture medium comprising a basal medium suitable for culturing plant cells supplemented with one or more auxins, one or more cytokinins and one or more agents which reduce oxidative browning, wherein the one or more agents which reduce oxidative browning are present in the medium at a concentration sufficient to prevent or reduce oxidative browning of the sorghum tissue; and wherein the one or more auxins and the one or more cytokinins are present in the medium in amounts relative to one another sufficient to produce DECs from the IEs during culture.

In one example, the one or more agents which reduce oxidative browning are selected from the group consisting of lipoic acid, melatonin, 2-aminoidan-2-phosphonic acid, ascorbic acid, alpha-tocopherol, 3,5-dibutyl-4-hydroxytoluene (BHT), cysteine, selenite, polyvinylpolypyrrolidone (PVPP), dithiothreitol (DTT), phenoxane, silver nitrate, citrate, glutathione, phytic acid, nordihydroguaiaretic acid (NDGA), and activated charcoal. Preferably the agent which reduces oxidative browning is lipoic acid e.g., α-lipoic acid.

In one example, the one or more agents which reduce oxidative browning are present at a concentration of about 0.1 mg/L to about 10 mg/L, about 0.5 g/L to about 5 g/L, about 1 g/L to about 5 g/L, or about 1 g/L. Preferably, the one or more agents which reduce oxidative browning are present at a concentration of about 1 mg/L.

In one example, the one or more auxins are selected from the group consisting of indole-3-acetic acid (IAA), 4-chlor-oindole-3-acetic acid, phenylacetic acid, indole-3-butyric acid (IBA), 1-naphthaleneacetic acid (NAA), 2-naphthoxy-acetic acid, 4-chlorophenoxyacetic acid, 2,4-dichlorophenoxyacetic acid (2,4-D), 2,4,5-Trichlorophenoxyacetic acid, 2,3,5-Triiodobenzoic acid, picloram, and salt forms of any one thereof. Preferably the auxin is 2,4-D.

In one example, the one or more auxins are present at a concentration of about 0.1 mg/L to about 5 mg/L, about 0.1 mg/L to about 3 mg/L, about 0.3 mg/L to about 2 mg/L, about 0.5 mg/L to about 1 mg/L or about 1 mg/L. Preferably, the one or more auxins are present at a concentration of about 1 mg/L.

In one example, the one or more cytokinins are selected from the group consisting of benzylaminopurine (BAP), zeatin, kinetin, 21P, zeatin riboside, diphenylurea and thidiazuron (TDZ). In a preferred example, the cytokinin is BAP.

In one example, the one or more cytokinins are present at a concentration of about 0.01 mg/L to about 2 mg/L, about 0.1 mg/L to about 2 mg/L, about 0.5 mg/L to about 2 mg/L, about 0.5 mg/L to about 1 mg/L, or about 0.5 mg/L. Preferably, the one or more cytokinins are present at a concentration of about 0.5 mg/L.

In one example, the one or more auxins and the one or more cytokinins are present in medium at a weight ratio (auxin:cytokinin) of about 1.25:1, about 1.5:1, about 1.75:1, about 2:1, about 2.25:1, about 2.5:1, about 2.75:1, or about 3:1.

In one example, the agent which reduces oxidative browning is lipoic acid e.g., α-lipoic acid, and the lipoic acid is present in the medium at a concentration of about 0.5 mg/L to about 2.0 mg/L, or about 1 mg/L. Preferably, the lipoic acid e.g., α-lipoic acid, is present in the medium at a concentration of about 1 mg/L.

In one example, the culture medium comprises peptone. For example, the peptide is present at a concentration of about 0.2 g/L to about 2 g/L, about 0.5 g/L to about 1.5 g/L, about 0.7 g/L to about 1 g/L, or about 0.8 g/L. In one example, peptone is present in the culture medium at a concentration of about 0.8 g/L.

In one example, the culture medium comprises a source of copper. For example, the culture medium comprises cupric sulfate, copper chloride, copper nitrate, copper gluconate, or copper acetate.

In one example, the culture medium comprises copper at a concentration of about 0.1 mg/L to about 5 mg/L, about 0.3 mg/L to about 3 mg/L, about 0.5 mg/L to about 1.5 mg/L, about 0.7 mg/L to about 1 mg/L, or about 0.8 mg/L.

In one example, the culture medium comprises an osmotic agent.

In one example, the culture medium comprises a solidifying agent e.g., agar.

In one example, the basal media is MS media.

In one example, the culture medium which is suitable for use in producing DEC tissue of sorghum comprises MS media at a concentration of about 4 g/L to about 5 g/L, 2,4-D at a concentration of about 1 mg/L, BAP at a concentration of about 0.5 mg/L and lipoic acid at a concentration of about 1 mg/L. In addition, the culture media may comprise one or more or all of L-proline at a concentration of about 0.5 g/L to about 1 g/L, peptone at a concentration of about 0.5 g/L to about 1 g/L, myo-inositol at a concentration of about 100 mg/L to about 200 mg/L, copper sulfate at a concentration of about 0.5 g/L to about 1 g/L, maltose at a concentration of about 10 g/L to about 50 g/L, and agar at a concentration of about 6 g/L to about 12 g/L.

In one example, the culture medium has a pH which is suitable for producing DEC tissue. For example, the culture media has a pH of about pH 5.0 to about pH 6.0.

Also provided is the culture medium as described herein when used to prepare DEC tissue of sorghum e.g., in a method described herein.

The present disclosure also provides a differentiating embryogenic callus (DEC) tissue of sorghum capable of being genetically modified with an efficiency of at least 35%. In one example, the DEC tissue is capable of being genetically modified with an efficiency of at least 40%. In one example, the DEC tissue is capable of being genetically modified with an efficiency of at least 45%. In one example, the DEC tissue is capable of being genetically modified with an efficiency of at least 50%. In one example, the DEC tissue is capable of being genetically modified with an efficiency of at least 55%. In one example, the DEC tissue is capable of being genetically modified with an efficiency of at least 60%. In one example, the DEC tissue is capable of being genetically modified with an efficiency of at least 65%. In one example, the DEC tissue is capable of being genetically modified with an efficiency of at least 70%. In one example, the DEC tissue is capable of being genetically modified with an efficiency of at least 75%. In one example, the DEC tissue is capable of being genetically modified with an efficiency of at least 80%. In one example, the DEC tissue is capable of being genetically modified with an efficiency of at least 85%. In one example, the DEC tissue is capable of being genetically modified with an efficiency of at least 90%.

In one example, wherein the genetic modification efficiency is as determined by performing a method of producing a genetically modified sorghum plant according to the method disclosed herein using the DEC tissue and calculating the efficiency of genetic modification.

In one example, the DEC tissue is produced and/or provided in the culture media which is suitable for producing a DEC cell as disclosed herein.

Any embodiment herein shall be taken to apply mutatis mutandis to any other embodiment unless specifically stated otherwise.

The present invention is not to be limited in scope by the specific embodiments or examples described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples.

DETAILED DESCRIPTION OF THE INVENTION

General Techniques and Definitions

Figure 1:
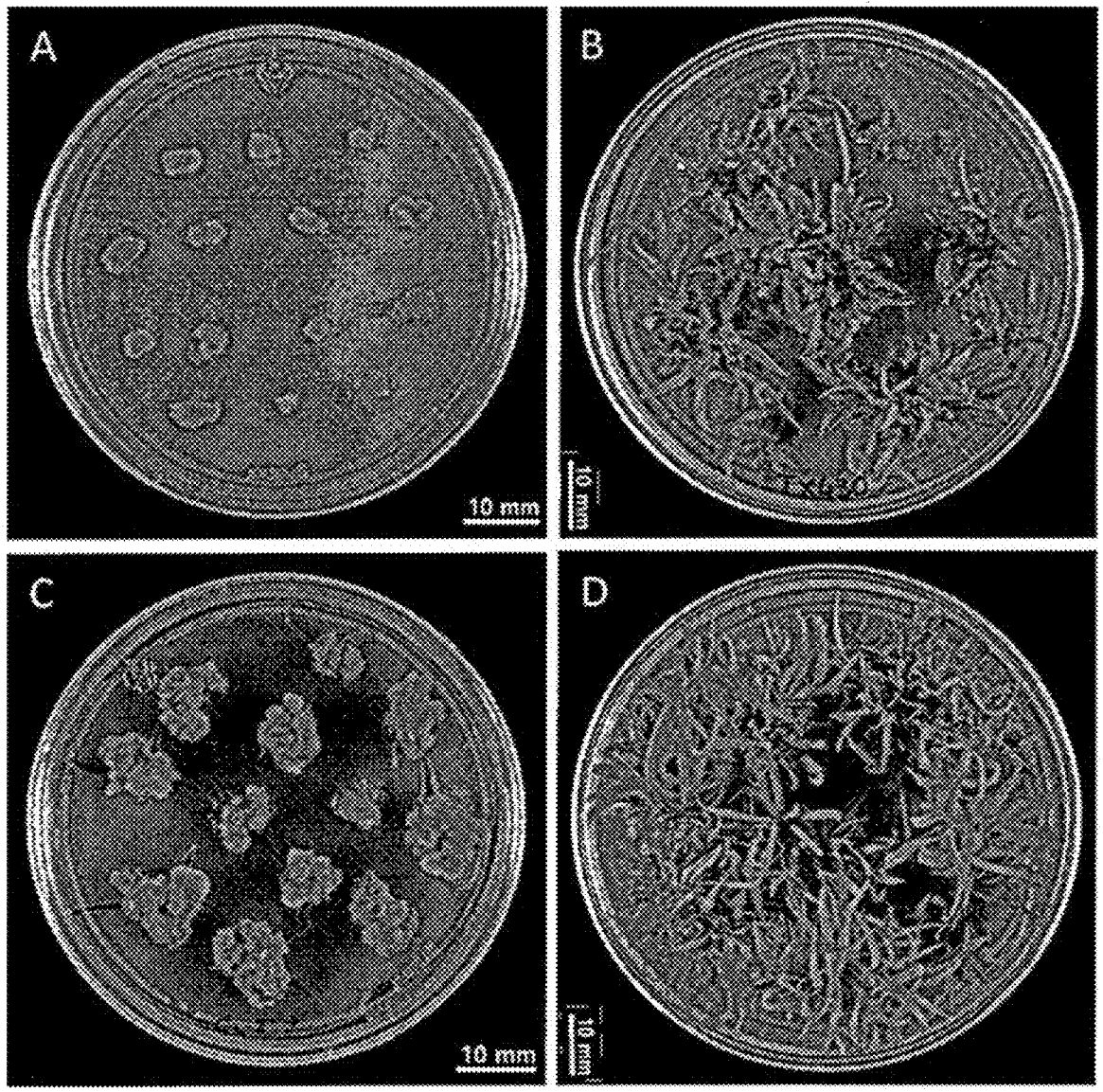
FIG. 1. Generation of DEC tissue and plant regeneration from immature embryos of Sorghum: (A) Callus initiation from embryo (3 week old); (C) Embryogenic callus with nodular structures (~8 weeks old); (B) & (D) Shoot induction without and with LA in SIM and SRM, respectively.

Unless specifically defined otherwise, all technical and scientific terms used herein shall be taken to have the same meaning as commonly understood by one of ordinary skill in the art (e.g., in cell culture, plant transformation, molecular genetics, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present).

The term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−10%, more preferably +/−5%, more preferably +/−1% of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The present disclosure relates generally to Sorghum, and includes inter alia methods and materials for genetically modifying Sorghum. As used herein, the term "Sorghum" refers to a genus of numerous species of annual cereal grasses having broad leaves and a tall, pithy stem bearing the grain in a dense terminal cluster. It is contemplated that the methods, tissues and mediums disclosed herein may be used with any Sorghum sp. including, but not limited to, *Sorghum bicolor, Sorghum halepense, Sorghum almum, Sorghum sudanense,* and *Sorghum propinquum. Sorghum bicolor* is the primary cultivated Sorghum species and include a number of different types are recognized, including grain sorghums, sweet sorghums, grass sorghums, and broom corn, all of which are contemplated according to the present teachings. According to a specific embodiment, the sorghum is grain sorghum or sweet sorghum. Furthermore, it is contemplated that the methods, tissues and mediums disclosed herein may be used with any sorghum line or variety including, but are not limited to, public lines such as CS3541, M91051, SRN39, Shanqui red, IS8260, IS4225, Tx430, P898012, P954035 and PP290.

Methods of Producing DEC Tissue of Sorghum

As discussed herein, immature embryos have been the choice of explant for transformation of sorghum to date. One of the factors that has hampered transformation efficiencies of sorghum with the immature embryos as explants is the rapid production of phenolic compounds in tissue culture. Another disadvantage of using immature embryos directly as explant is the need for continued planting of stock plants to ensure a constant supply of immature embryos which is difficult due to the flowering occurs for few days only, thereby providing a small window for collection of most appropriate embryos. In addition to labour and cost to the system, the donor plant physiological condition will have an impact on the quality of the embryo which can influence the callus initiation frequency from the transformed cell. The present disclosure is based, in part, on recognition by the inventors that differentiating embryogenic callus (DEC) tissue of sorghum induced from isolated immature embryos from sorghum provides a more flexible choice of explant for transformation of sorghum, particularly as DEC tissue is independent of environmental factors. As described herein, the inventors have shown that when used as an explant for transformation of sorghum, DEC tissue can achieve improved transformation efficiency relative to immature embryos.

Thus, in one example, the present disclosure relates to a method for preparing differentiating embryogenic callus (DEC) tissue of sorghum. As used herein, the term "differentiating embryogenic callus tissue" or "DEC tissue" shall be taken to mean tissue comprising nodular structures of differentiating cells which maintain embryogenic and organogenic potential. The "Differentiating embryogenic callus tissue" or "DEC tissue" may be comprised of a population of cells made up of callus cells, cells forming nodular structures and granular structures, intermediate cells which are on the developmental pathway somewhere between callus (which is undifferentiated cells) and nodular structures, and/or early stage (globular) somatic embryos. As used herein, cells which "maintain embryogenic potential" shall be understood to mean cells which are capable of undergoing the process of embryogenesis, a process by which shoots and roots develop together in a concerted fashion (not sequentially), whether from somatic cells or gametes. As used herein, cells which "maintain organogenic potential" shall be understood to mean cells which are capable of undergoing the process of organogenesis, a process by which shoots and roots are developed sequentially from meristematic centers. The process of "organogenesis" shall be understood to include a series of organized integrated processes that transform undifferentiated cells into a complete organ (i.e., shoot, leaf, root etc.) in a developing plant. The cells of an organ-forming region undergo differential development to form an organ primordium. Organogenesis continues until the definitive characteristics of the organ are achieved.

In one example, the method of producing DEC tissue comprises culturing isolated immature embryos (IEs) obtained from sorghum in callus inducing medium (CIM) for a time and under conditions sufficient to produce DEC tissue from the IEs, wherein the CIM comprises a basal medium suitable for culturing plant cells supplemented with one or more auxins, one or more cytokinins and one or more agents which reduce oxidative browning e.g., of sorghum tissue. In one example, the basal medium is MS medium.

As used herein, the term "immature embryo" or "IE" or variations thereof refers to an embryo of an immature seed i.e., of sorghum, that is under maturation following pollination but that is not yet capable of germination into a sorghum plant, and includes embryos in early stage development i.e., pre-cotyledonary embryos, and mid-stage development i.e., embryos with cotyledons or hypocotyls that are not yet fully developed.

As used herein, the term "agent which reduces oxidative browning" or similar shall be understood to mean a compound which prevents, inhibits or otherwise reduces a level of oxidative browning of sorghum tissue in culture, relative to a level of oxidative browning of the sorghum tissue which would otherwise occur in culture in the absence of the compound, as a result of the production of polyphenols by the sorghum tissue in the culture. Compounds which inhibit oxidative browning of plant tissue and which are suitable for use in the method and culture medium of the present disclosure will be known to the skilled person and are described herein. For example, the one or more agents which reduce oxidative browning may be selected from the group consisting of lipoic acid, melatonin, 2-aminoidan-2-phosphonic acid, ascorbic acid, alpha-tocopherol, 3,5-dibutyl-4-hydroxytoluene (BHT), cysteine, selenite, polyvinylpolypyrrolidone (PVPP), dithiothreitol (DTT), phenoxane, silver nitrate, citrate, glutathione, phytic acid, nordihydroguaiaretic acid (NDGA), and activated charcoal. In a preferred example, the CIM comprises lipoic acid e.g., α-lipoic acid, as an agent for reducing oxidative browning of sorghum tissue.

Preferably, the CIM will comprise the one or more agent which reduce oxidative browning in an amount sufficient to reduce a level of oxidative browning of sorghum tissue in culture, for example, by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, relative to a level of oxidative browning of the sorghum tissue which would otherwise occur in culture in the absence of the compound. In one example, the one or more agents which reduce oxidative browning are present in an amount sufficient to substantial inhibit or prevent oxidative browning of the sorghum tissue in culture. For example, the CIM may comprise the one or more agents which reduce oxidative browning of sorghum tissue at a concentration of about 0.1 mg/L to about 5 mg/L, about 0.5 g/L to about 5 g/L, about 1 g/L to about 5 g/L, or about 1 g/L. In one example, the CIM may comprise the one or more agents which reduce oxidative browning of sorghum tissue at a concentration of about 0.5 mg/L to about 2.0 mg/L, or about 1 mg/L. In one example, the CIM comprises lipoic acid e.g., α-lipoic acid, at a concentration of about 0.5 mg/L to about 2.0 mg/L e.g., at a concentration of about 1 mg/L.

As used herein, the term "auxin" refers to a class of plant growth regulatory compounds which stimulate cellular elongation and division, differentiation of vascular tissue, fruit development, formation of adventitious roots, production of ethylene, and (in high concentrations) induce dedifferentiation (callus formation). Suitable auxins for use in the method and culture medium of the present disclosure will be known to the skilled person and are described herein. For example, suitable auxins may be selected from the group consisting of indole-3-acetic acid (IAA), 4-chloroindole-3-acetic acid, phenylacetic acid, indole-3-butyric acid (IBA), 1-naphthaleneacetic acid (NAA), 2-naphthoxyacetic acid, 4-chlorophenoxyacetic acid, 2,4-dichlorophenoxyacetic acid (2,4-D), 2,4,5-Trichlorophenoxyacetic acid, 2,3,5-Triiodobenzoic acid, picloram, and salt forms of any one thereof.

Preferably, the CIM will comprise the one or more auxins in an amount sufficient to induce and/or stimulate cellular differentiation, whilst maintaining embryogenic and organogenic potential of the sorghum tissue. For example, CIM may comprise auxin at a concentration of about 0.1 mg/L to about 5 mg/L, about 0.1 mg/L to about 3 mg/L, about 0.3 mg/L to about 2 mg/L, or about 0.5 mg/L to about 1 mg/L. In one example, the CIM comprises 2,4-D at a concentration of about 1 mg/L.

The term "cytokinin" as used herein refers to a class of plant growth regulatory compounds which stimulate cellular division, expansion of cotyledons, and growth of lateral buds. They delay senescence of detached leaves and, in combination with auxins (described herein) may influence formation of roots and shoots. Suitable cytokinins for use in the method and culture medium of the present disclosure will be known to the skilled person and are described herein. For example, suitable cytokinins for inclusion in the CIM may be selected from the group consisting benzylaminopurine (BAP), zeatin, kinetin, 21P, zeatin riboside, diphenylurea and thidiazuron (TDZ).

Preferably, the CIM will comprise the one or more cytokinins in an amount sufficient to induce and/or stimulate cellular division of the sorghum tissue. For example, CIM may comprise the one or more cytokinins at a concentration of about 0.01 mg/L to about 2 mg/L, about 0.1 mg/L to about 2 mg/L, about 0.5 mg/L to about 2 mg/L, about 0.5 mg/L to about 1 mg/L, or about 0.5 mg/L. In one example, the CIM comprises BAP at a concentration of about 0.5 mg/L.

A skilled person will appreciate that the "callus-induction medium" or "CIM" is thus formulated to comprise auxin and cytokinin in relative amounts sufficient to induce and stimulate growth of nodular structures of differentiating cells which maintain embryogenic and organogenic potential, but without allowing substantial differentiation of the sorghum tissue into organized structures. In one example, the one or more auxins and the one or more cytokinins are present in the CIM at a weight ratio (auxin:cytokinin) of about 1.25:1, about 1.5:1, about 1.75:1, about 2:1, about 2.25:1, about 2.5:1, about 2.75:1, or about 3:1.

A particularly preferred example of a CIM which is useful for producing DEC tissue in a method of the disclosure comprises substantially the same concentration of auxin, cytokinin and agent for reducing oxidative browning, as the CIM described in Table 1 of Example 1. Alternatively, or in addition, a CIM which is useful for producing DEC tissue in a method of the disclosure comprises the same auxin, cytokinin and agent for reducing oxidative browning, as the CIM described in Table 1 of Example 1. A particularly preferred example of a CIM which is useful for producing DEC tissue in a method of the disclosure is described in Table 1 of Example 1. Accordingly, the CIM which is useful for producing DEC tissue in a method of the disclosure can comprise the agent for reducing oxidative browning, the auxin and the cytokinin of the CIM as described in Table 1, optionally wherein any one of more of the agent for reducing oxidative browning, the auxin and the cytokinin are present at the same concentration as the CIM described in Table 1. The CIM which is useful for producing DEC tissue in a method of the disclosure can further comprise any one of more or all of the other constituents of the CIM described in Table 1, optionally at the same concentration as the CIM described in Table 1.

In one example, the CIM comprises BAP at a concentration of about 0.5 mg/L, 2,4-D at a concentration of about 1 mg/L and lipoic acid e.g., α-lipoic acid, at a concentration of about 1 mg/L.

The CIM as employed during the method of the disclosure may comprise one or more other constituents which are known to be useful in plant tissue culture, including sources of macronutrients, micronutrients, vitamins, amino acids or nitrogen supplements, source(s) of carbon, undefined organic supplements, and solidifying agents. In one example, the CIM of the disclosure comprises (in addition to an auxin, cytokinin and agent for reducing oxidative browning), peptone, a source of copper, an osmotic agent and/or a solidifying agent.

For example peptone may be a included in the CIM as source of nitrogen, vitamins and/or amino acids. In one example, peptone is be included in the CIM of the disclosure at a concentration of about 0.2 g/L to about 2 g/L, about 0.5 g/L to about 1.5 g/L, about 0.7 g/L to about 1 g/L, or about 0.8 g/L. In one example, peptone is present in the CIM at a concentration of about 0.8 g/L.

Copper is required for activation of certain enzymatic pathways in plants e.g., such as those involved in lignin synthesis. It is also required for photosynthesis, plant respiration and assists in plant metabolism of carbohydrates and proteins. Thus, in one example, the CIM used in the method of the disclosure may comprise a source of copper. For example, the CIM may comprise copper in the form of cupric sulfate, copper chloride, copper nitrate, copper gluconate, or copper acetate. The copper may be present in the CIM at a concentration of about 0.1 mg/L to about 5 mg/L, about 0.3 mg/L to about 3 mg/L, about 0.5 mg/L to about 1.5 mg/L, about 0.7 mg/L to about 1 mg/L, or about 0.8 mg/L.

The CIM may comprise an osmotic agent. Suitable osmotic agents for use in plant cell culture are known in the art and contemplated for use in the CIM described herein. For example, an osmotic for inclusion in the CIM of the disclosure may be selected from myo-inositol, sucrose, mannitol, glycerol, sorbitol and maltose.

Solidifying agents useful in plant cell culture medium are known in the art e.g., agar, and are also contemplated for use in the CIM described herein.

A particularly preferred example of a CIM which is useful for producing DEC tissue in a method of the disclosure is described in Table 1 of Example 1. Accordingly, the CIM which is useful for producing DEC tissue in a method of the disclosure can comprise the agent for reducing oxidative browning, the auxin and the cytokinin of the CIM as described in Table 1, optionally wherein any one of more of the agent for reducing oxidative browning, the auxin and the cytokinin are present at the same concentration as the CIM described in Table 1. The CIM which is useful for producing DEC tissue in a method of the disclosure can further comprise any one of more or all of the other constituents of the CIM described in Table 1, optionally at the same concentration as the CIM described in Table 1.

In one example, the method of producing DEC tissue as described herein comprises culturing the IEs obtained from sorghum in CIM under dim light conditions for a time sufficient to produce the DEC tissue from the IEs. As used herein, the term "dim light conditions" refers to conditions comprising light e.g., white light, irradiated at an intensity from about 10 mol m$^{-2}$ sec$^{-1}$ to about 55 µmol m$^{-2}$ sec$^{-1}$.

According to one example, the method of the disclosure comprise culturing of the IEs under dim light conditions having a light intensity of about 10 µmol s$^{-1}$ m$^{-2}$ to about 55 µmol s$^{-1}$ m$^{-2}$, or about 30 µmol s$^{-1}$ m$^{-2}$ to about 50 mol s$^{-1}$ m$^{-2}$, or about 45 µmol s$^{-1}$ m$^{-2}$ to about 50 µmol s$^{-1}$ m$^{-2}$. In one particular example, the dim light conditions used to culture the IEs, and thereby produce DEC tissue, comprises white light irradiated at an intensity of about 30 µmol m$^{-2}$ sec$^{-1}$ to about 45 µmol m$^{-2}$ sec-1.

As described herein, it is anticipated that the culturing of the IEs obtained from sorghum occurs for an amount of time sufficient to produce the DEC tissue from the IEs. A skilled person will appreciate that growth of a plant or plant tissue, particularly green tissue, will be influenced by photoperiod, as well as the period of culturing if the tissue. As used herein, the term "photoperiod" shall be understood to mean the duration of light exposure that a plant or tissue e.g., a sorghum plant or tissue, has received in a 24-hour period.

In each of the forgoing examples, it is contemplated that culturing under dim light conditions may occur with a photoperiod of about 12 h to about 20 hours, about 14 h to about 18 hours, or about 14 h to about 16 hours. For example, culturing under dim light conditions may occur with a photoperiod of about 12 h, about 14 h, about 16 h, about 18 h, or about 20 h. In a preferred example, culturing under dim light conditions in accordance with the method of the disclosure occurs with a photoperiod of about 14 h to about 16 hours e.g., 16 h. In accordance with any example hereof, the time sufficient to produce the DEC tissue from the IEs may be about 2 to about 6 weeks, about 3 to about 5 weeks, or about 4 weeks.

Once DEC tissue has been obtained by the method described herein, it is contemplated that one or more subculture steps may take place in order to maintain a fresh population of DEC tissue of sorghum. One advantage of maintaining one or more populations of DEC tissue by performing a subculture step is the provision of a continuous supply of fresh DEC tissue, including at a time of year when it is difficult to obtain immature embryos from flowering sorghum plants.

Accordingly, the method of producing DEC tissue as described herein may include one or more subculturing steps. As used herein, the term "subculture" refers to the process of transferring a portion of tissue or cells from an existing culture, to a new culture vessel containing fresh culture medium and resuming culturing of the tissue or cells. Each round of subculture may be referred to a "passage" of the cells or tissue. Thus, when cells or tissue are subcultured, they can also be referred to as having been passaged.

In accordance with the method described herein, the one or more subculturing step(s) may comprise transferring DEC tissue obtained by the method described herein to a different culture vessel comprising fresh CIM and exposing the subculture to substantially the same conditions used to produce the DEC tissue from the IEs. In accordance with one example, a subculture step is performed every 2 to 4 weeks to maintain the DEC tissue. For example, the DEC tissue may be subcultured about every 2 weeks. For example, the DEC tissue may be subcultured about every 3 weeks. For example, the DEC tissue may be subcultured about every 4 weeks. According to any one of the foregoing examples in which the method of producing DEC tissue comprises one or more subculture steps, the subculture step may be repeated to maintain the DEC tissue for at least 4 months, at least 5 months, at least 6 months, at least 7 months, at least 8 months and/or up to 12 months from the time that the DEC tissue was produced from the IEs. In this regard, an advantage of the method of the disclosure is that the DEC tissues produce may be maintained for up to, or greater than, 6 months by performing subcultures.

Methods of Genetically Modifying Sorghum

As described herein, when used as an explant for transformation of sorghum, DEC tissue of the disclosure can achieve improved transformation efficiency relative to that achieved when immature embryos are used as an explant tissue for transformation.

Accordingly, a further aspect of the disclosure relates to a method of producing a genetically modified sorghum cell, said method comprising introducing one or more nucleic acids into a cell of DEC tissue of sorghum.

The present disclosure also relates to a method of producing a genetically-modified sorghum plant or regenerative part thereof, comprising in order:
(a) performing the method of producing a genetically modified sorghum cell on one or more DEC tissues as described herein;
(b) culturing the DEC tissue(s) into which the one or more nucleic acids have been introduced on a medium, or a series of media, such that said culturing induces shoot formation from the DEC tissue(s), thereby producing one or more genetically modified shoot;
(c) producing one or more genetically modified sorghum plants from the genetically modified shoot of step (b), thereby producing the genetically-modified sorghum plant(s); and optionally
(d) obtaining regenerative parts from the genetically modified plant(s) of step (c).

The present disclosure also relates to a method of producing a genetically-modified sorghum plant or regenerative part thereof, comprising in order:
(a) introducing one or more nucleic acids into a population of sorghum tissues;
(b) culturing the sorghum tissues into which the one or more nucleic acids have been introduced on a medium, or a series of media, such that said culturing induces shoot formation from said sorghum tissues at an efficiency of at least 35 genetically modified shoots per 100 sorghum tissues into which the one or more nucleic acids has been introduced, thereby producing genetically modified shoots; and (c) producing one or more genetically modified sorghum plants from the genetically-modified shoots of step (b), thereby producing the genetically modified sorghum plant(s); and optionally (d) obtaining a regenerative part from the genetically modified plant(s) of step (c).

In one example, an efficiency of at least 40 genetically modified shoots per 100 sorghum tissues into which the one or more nucleic acids has been introduced, is achieved. In one example, an efficiency of at least 45 genetically modified shoots per 100 sorghum tissues into which the one or more nucleic acids has been introduced, is achieved. In one example, an efficiency of at least 50 genetically modified shoots per 100 sorghum tissues into which the one or more nucleic acids has been introduced, is achieved. In one example, an efficiency of at least 55 genetically modified shoots per 100 sorghum tissues into which, the one or more nucleic acids has been introduced, is achieved. In one example, an efficiency of at least 60 genetically modified shoots per 100 sorghum tissues into which the one or more nucleic acids has been introduced, is achieved. In one example, an efficiency of at least 65 genetically modified shoots per 100 sorghum tissues into which the one or more nucleic acids has been introduced, is achieved. In one example, an efficiency of at least 70 genetically modified shoots per 100 sorghum tissues into which the one or more nucleic acids has been introduced, is achieved. In one example, an efficiency of at least 75 genetically modified shoots per 100 sorghum tissues into which the one or more nucleic acids has been introduced, is achieved. In one example, an efficiency of at least 80 genetically modified shoots per 100 sorghum tissues into which the one or more nucleic acids has been introduced, is achieved. In one example, an efficiency of at least 85 genetically modified shoots per 100 sorghum tissues into which the one or more nucleic acids has been introduced, is achieved. In one example, an efficiency of at least 90 genetically modified shoots per 100 sorghum tissues into which the one or more nucleic acids has been introduced, is achieved.

As used herein, the term "genetically modified", in the context of a sorghum cell, tissue, shoot or plant as described herein, refers to a sorghum cell, tissue, shoot or plant whose genetic material i.e., DNA, has been altered e.g., by the addition of DNA, the deletion of DNA or the substitution of DNA. In some examples, a sorghum cell, tissue, shoot or plant which has been "genetically modified" in accordance with the method described herein is modified to contain a gene (or part thereof) found in a wild-type sorghum plant, variety or cultivar e.g., such as a favourable gene variant from an elite line or genetically distinct population. In another example, a sorghum cell, tissue, shoot or plant which has been "genetically modified" in accordance with the method described herein is modified to contain a gene construct ("transgene") or other heterologous polynucleotide not found in a wild-type sorghum plant, variety or cultivar. A sorghum cell, tissue or plant which has been "genetically modified" by introduction of a transgene or heterologous polynucleotide may be referred to as being "transgenic". A "transgene" as referred to herein has the normal meaning in the art of biotechnology and includes a genetic sequence which has been produced or altered by recombinant DNA or RNA technology and which has been introduced into a cell.

The term "regenerative part" in the context of a genetically modified plant of the disclosure refers to a reproductive part which is capable of giving rise to a sorghum plant e.g., such as a seed or embryo. As used herein, the term "seed" refers to "mature seed" of a plant, which is either ready for harvesting or has been harvested from the plant, such as is typically harvested commercially in the field, or as "developing seed" which occurs in a plant after fertilisation and prior to seed dormancy being established and before harvest.

The term "introducing", as used in the context of a nucleic acid, means presenting the nucleic acid to sorghum DEC tissue or sorghum tissue in such a manner that the nucleic acid gains access to the interior of a cell in the DEC tissue or sorghum tissue. Where more than one nucleic acid is to be introduced using the method of the disclosure, these nucleic acid can be assembled as part of a single nucleic acid construct, or as separate nucleic acid constructs, and can be located on the same or different transformation vectors. Accordingly, multiple nucleic acid can be introduced into DEC tissue in a single transformation event, in separate transformation events, or, e.g., as part of a breeding protocol.

The term "transformation" as used herein refers to the introduction of a nucleic acid into a cell of DEC tissue or other sorghum tissue explant. Transformation of the cell may be stable or transient.

The one or more nucleic acids may be introduced to cells of the DEC tissue, or other sorghum tissue explant, by any means known in the art. Four general methods for direct delivery of nucleic acids into cells have been described: (1) chemical methods (Graham et al., 1973); (2) physical methods such as microinjection (Capecchi, 1980); electroporation (see, for example, WO 87/06614, U.S. Pat. Nos. 5,472,869, 5,384,253, WO 92/09696 and WO 93/21335); and the gene gun (see, for example, U.S. Pat. Nos. 4,945,050 and 5,141,131); (3) viral vectors (Clapp, 1993; Lu et al., 1993; Eglitis et al., 1988); and (4) receptor-mediated mechanisms (Curiel et al., 1992; Wagner et al., 1992).

Acceleration methods that may be used include, for example, microprojectile bombardment and the like. One example of a method for delivering one or more nucleic acids to cells of DEC tissue, or cells of other sorghum tissue explant, is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required. An illustrative embodiment of a method for delivering DNA into *Zea mays* cells by acceleration is a biolistics α-particle delivery system, that can be used to propel particles coated with DNA through a screen, such as a stainless steel or Nytex screen, onto a filter surface covered with corn cells cultured in suspension. A particle delivery system suitable for use with the present invention is the helium acceleration PDS-1000/He gun is available from Bio-Rad Laboratories.

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, the sorghum DEC tissue or other sorghum tissue explant may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus that express the exogenous gene product 48 hours post-bombardment often range from one to ten and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids.

In another alternative example, plastids can be stably transformed. Methods disclosed for plastid transformation in higher plants include particle gun delivery of DNA containing a selectable marker and targeting of the DNA to the plastid genome through homologous recombination (U.S. Pat. Nos. 5,451,513, 5,545,818, 5,877,402, 5,932,479, and WO 99/05265).

Accordingly, it is contemplated that one may wish to adjust various aspects of the bombardment parameters in small scale studies to fully optimize the conditions. One may particularly wish to adjust physical parameters such as gap distance, flight distance, tissue distance, and helium pressure. One may also minimize the trauma reduction factors by modifying conditions that influence the physiological state of the recipient cells and that may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-mediated transfer is a widely applicable system for introducing nucleic acids into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art (see, for example, U.S. Pat. Nos. 5,177,010, 5,104,310, 5,004,863, 5,159,135). Further, the integration of the T-DNA is a relatively precise process resulting in few rearrangements. The region of DNA to be transferred is defined y the border sequences, and intervening DNA is usually inserted into the plant genome.

Modern *Agrobacterium* transformation vectors are capable of replication in *E. coli* as well as *Agrobacterium*, allowing for convenient manipulations as described (Klee et al., In: Plant DNA Infectious Agents, Hohn and Schell, eds., Springer-Verlag, New York, pp. 179-203 (1985). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations.

A genetically modified plant or tissue formed using *Agrobacterium* transformation methods typically contains a single genetic locus on one chromosome. Such transgenic plants can be referred to as being hemizygous for the added nucleic acid. More preferred is a genetically modified plant that is homozygous for the added nucleic acid; i.e., one nucleic acid at the same locus on each chromosome of a chromosome pair. A homozygous genetically modified plant can be obtained by sexually mating (selfing) an independent segregant genetically modified plant that contains a single added nucleic acid, germinating some of the seed produced and analyzing the resulting plants for the nucleic acid of interest.

In a preferred example, the one or more nucleic acids introduced to the DEC tissue or sorghum tissue using the method of the disclosure are stably introduced.

As used herein, the term "stably introducing" or "stably introduced", in the context of a nucleic acid introduced into a sorghum cell, is intended to mean that the introduced nucleic acid is stably incorporated into the genome of the sorghum cell, and thus the cell is stably transformed with the nucleic acid. As used herein, the term "stable transformation" or "stably transformed" means that a nucleic acid is introduced into a cell and integrates into the genome of the cell. As such, the integrated nucleic acid is capable of being inherited by the progeny thereof, more particularly, by the progeny of multiple successive generations. As referred to herein, the term "genome" includes the nuclear and the plastid genome, and therefore includes integration of the nucleic acid into, for example, the chloroplast genome. Stable transformation as used herein can also refer to a nucleic acid that is maintained extrachromasomally, for example, as a minichromosome.

A genetically modified sorghum plant produced from DEC tissue, or other sorghum explant, into whose genome a nucleic acid has been integrated using a method of the disclosure may be referred to as a "germline stably-transformed sorghum plant".

A "nucleic acid" as used herein shall be understood to mean a polynucleotide such as, for example, DNA, RNA or oligonucleotides. The one or more nucleic acids introduced to the DEC tissue or sorghum tissue may be present in one or more nucleic acid constructs, such as expression cassettes, capable of directing expression of a particular polynucleotide sequence in the nucleic acid in a sorghum plant, and will generally comprise a promoter operatively-linked to the polynucleotide sequence and/or one or more other regulatory elements required for proper expression and translation of a protein or polypeptide encoded thereby.

Preferably, the one or more nucleic acids introduced into the DEC tissue or sorghum tissue may comprise at least one gene of interest. The gene of interest may increase or decrease the endogenous level of activity of a protein in the genetically modified sorghum plant or tissue or regenerative part thereof, or may introduce a new protein to the sorghum plant, tissue or regenerative part thereof. For example, the gene of interest may encode a protein or functional polynucleotide which; increases yield, confers enhanced animal and/or human nutrition, confers herbicide tolerance (e.g. glyphosate resistance or glufosinate resistance), affects carbohydrate biosynthesis or modification (e.g. starch branching enzyme, starch debranching enzyme, starch synthases, ADP-glucose pyrophosphorylase), is involved in fatty acid biosynthesis or modification (e.g. a desaturase, elongase, hydroxylase, epoxidase, conjugase, acetylase, TAG assembly), confers insect resistance (e.g. crystal toxin protein of *Bacillus thuringiensis*), confers viral resistance (e.g. viral coat protein); confers fungal resistance (e.g. chitinase, β-1, 3-glucanase, moricin-related peptides or phytoalexins), alters sucrose metabolism (e.g. invertase or sucrose synthase), confers reduced allergenicity, increases digestibility, confers environmental stress tolerance, confers nematode resistance, is a gene encoding a pharmaceutical (e.g. antibiotics, antibodies, secondary metabolites, pharmaceutical peptides or vaccines), is a gene encoding an industrial enzyme, or increases the use of the sorghum plant or part thereof as a biofuel.

In another example, it is contemplated that the method comprises introducing at least nucleic acid(s), wherein the at least two nucleic acids are loci related to the clustered regulatory interspaced short palindromic repeats (CRISPR)/Cas system for inducing targeted genetic alterations.

The CRISPR system can be portable to plant cells by co-delivery of plasmids expressing the Cas endonuclease and the necessary crRNA components. The Cas endonuclease may be converted into a nickase to provide additional control over the mechanism of DNA repair (Cong et al., 2013).

CRISPR loci are a distinct class of interspersed short sequence repeats (SSRs) that were first recognized in *E. coli* (Ishino et al., 1987; Nakata et al., 1989). Similar interspersed SSRs have, been identified in *Haloferax mediterranei, Streptococcus pyogenes, Anabaena*, and *Mycobacterium tuberculosis* (Groenen et al., 1993; Hoe et al., 1999; Masepohl et al., 1996; Mojica et al., 1995).

The CRISPR loci differ from other SSRs by the structure of the repeats, which have been termed short regularly spaced repeats (SRSRs) (Janssen et al., 2002; Mojica et al., 2000). The repeats are short elements that occur in clusters, that are always regularly spaced by unique intervening sequences with a constant length (Mojica et al., 2000). Although the repeat sequences are highly conserved between strains, the number of interspersed repeats and the sequences of the spacer regions differ from strain to strain (van Embden et al., 2000).

The common structural characteristics of CRISPR loci are described in Jansen et al. (2002) as (i) the presence of multiple short direct repeats, which show no or very little sequence variation within a given locus; (ii) the presence of non-repetitive spacer sequences between the repeats of similar size; (iii) the presence of a common leader sequence of a few hundred basepairs in most species harbouring multiple CRISPR loci; (iv) the absence of long open reading frames within the locus; and (v) the presence of one or more cas genes.

CRISPRs are typically short partially palindromic sequences of 24-40 bp containing inner and terminal inverted repeats of up to 11 bp. Although isolated elements have been detected, they are generally arranged in clusters (up to about 20 or more per genome) of repeated units spaced by unique intervening 20-58 bp sequences. CRISPRs are generally homogenous within a given genome with most of them being identical. However, there are examples of heterogeneity in, for example, the Archaea (Mojica et al., 2000).

As used herein, the term "cas gene" refers to one or more cas genes that are generally coupled associated or close to or in the vicinity of flanking CRISPR loci. A comprehensive review of the Cas protein family is presented in Haft et al. (2005). The number of cas genes at a given CRISPR locus can vary between species.

Thus, an embodiment in which loci of the CRISPR system are transformed into a DEC tissue or sorghum tissue using a method of the disclosure is contemplated to enable CRISPR mediated gene editing of the sorghum plant.

To facilitate identification of, or selection for transformants, the one or more nucleic acids may desirably comprise a "selectable marker gene". Accordingly, the method of producing a genetically modified sorghum cell or plant as described herein may comprise a selection for tissue or plants which have been transformed with the one or more nucleic acids.

The selectable marker gene may be comprised within a nucleic acid construct with the gene of interest, as described herein. However, these needn't be provided in the same nucleic acid construct, and the selectable marker gene may be provided separate to a nucleic acid comprising a gene of interest e.g., separate nucleic acid constructs.

By "selectable marker gene" is meant a gene that imparts a distinct phenotype to cells or tissue expressing the marker gene and thus allows such transformed cells or tissues to be distinguished from cells or tissues that do not have the marker. A selectable marker gene confers a trait for which one can "select" based on. For example, a selectable marker gene may confer resistance to a selective agent (e.g., a herbicide, antibiotic, radiation, heat, or other treatment damaging to untransformed cells). In accordance with an example in which the nucleic acid(s) comprise a selectable marker gene which confers resistance to a selective agent, the method comprises exposing the DEC tissue or sorghum tissue into which the nucleic acid(s) have been introduced (or a sorghum plant derived therefrom) to the corresponding selective agent.

Alternatively, or in addition, the one or more nucleic acids may comprise a selectable marker gene which confer a growth advantage to a transformant in the presence of a particular metabolite (e.g., trehalase gene, 3-glucoronidase (GUS) gene or phosphomannose isomerase (PMI) gene). In accordance with an example in which the nucleic acid(s) comprise a selectable marker gene which confers a growth advantage to a transformant in the presence of a particular metabolite, the method comprises culturing the DEC tissue or sorghum tissue into which the nucleic acid(s) have been introduced in the presence of the corresponding metabolite.

Alternatively, the selectable marker gene may be a "screenable marker gene" (or reporter gene) which confers a trait that one can identify through observation or testing, i.e., by "screening" (e.g., β-glucuronidase, luciferase, GFP or other enzyme activity not present in untransformed cells). In accordance with an example in which the nucleic acid(s) comprise a screenable marker gene, the method comprises culturing the DEC tissue or sorghum tissue into which the nucleic acid(s) have been introduced and selecting tissue, or a sorghum plant produced therefrom, that expresses the screenable marker gene (e.g., based on observable phenotype).

As described herein, the marker gene and the gene of interest do not have to be linked or provided in the same nucleic acid construct. Furthermore, the actual choice of a marker is not crucial as long as it is functional (i.e., selective) in combination with the DEC tissue or sorghum tissue used in the method of the disclosure. Further description of on exemplary selectable marker genes is provided herein.

In one example, a selectable marker suitable for use in a method described herein can be a fluorescent or bioluminescent marker. Examples of fluorescent or bioluminescent markers include, but are not limited to, green fluorescent protein (GFP), blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz, GFPuv, destabilised EGFP (dEGFP), destabilised ECFP (dECFP), destabilised EYFP (dEYFP), HcRed, t-HcRed, DsRed, DsRed2, t-dimer2, t-dimer2(12), mRFP1, pocilloporin, Renilla GFP, Monster GFP, paGFP, Kaede protein, a Phycobiliprotein, a luciferase, or a biologically active variant or fragment of any one thereof.

One very well-known example of fluorescent proteins includes the green fluorescent protein from the jellyfish Aequorea victoria and numerous other variants (GFPs) arising from the application of molecular biology, for example mutagenesis and chimeric protein technologies (Tsien, 1998). GFPs are classified based on the distinctive component of their chromophores, each class having distinct excitation and emission wavelengths: class 1, wild-type mixture of neutral phenol and anionic phenolate: class 2, phenolate anion: class 3, neutral phenol: class 4, phenolate anion with stacked s-electron system: class 5, indole: class 6, imidazole: and class 7, phenyl.

Light-emitting systems have been known and isolated from many luminescent organisms including bacteria, protozoa, coelenterates, molluscs, fish, millipedes, flies, fungi, worms, crustaceans, and beetles, particularly click beetles of genus Pyrophorus and the fireflies of the genera Photinus, Photuris, and Luciola. Additional organisms displaying bioluminescence are listed in WO 00/024878, WO 99/049019 and Viviani (2002).

One very well-known example is the class of proteins known as luciferases which catalyze an energy-yielding chemical reaction in which a specific biochemical substance, a luciferin (a naturally occurring fluorophore), is oxidized by an enzyme having a luciferase activity (Hastings, 1996). A great diversity of organisms, both prokaryotic and eukaryotic, including species of bacteria, algae, fungi, insects, fish and other marine forms can emit light energy in this manner and each has specific luciferase activities and luciferins which are chemically distinct from those of other organisms. Luciferin/luciferase systems are very diverse in form, chemistry and function. Bioluminescent proteins with luciferase activity are thus available from a variety of sources or by a variety of means. Examples of bioluminescent proteins with luciferase activity may be found in U.S. Pat. Nos. 5,229,285, 5,219,737, 5,843,746, 5,196,524, and 5,670,356. Two of the most widely used luciferases are: (i) Renilla luciferase (from R. renformis), a 35 kDa protein, which uses coelenterazine as a substrate and emits light at 480 nm (Lorenz et al., 1991); and (ii) Firefly luciferase (from Photinus pyralis), a 61 kDa protein, which uses luciferin as a substrate and emits light at 560 nm (de Wet et al., 1987).

Gaussia luciferase (from Gaussia princeps) has been used in biochemical assays (Verhaegen et al., 2002). Gaussia luciferase is a 20 kDa protein that oxidises coelenterazine in a rapid reaction resulting in a bright light emission at 470 nm.

Luciferases useful in the method of the disclosure have also been characterized from Anachnocampa sp (WO 2007/019634). These enzymes are about 59 kDa in size and are ATP-dependent luciferases that catalyze luminescence reactions with emission spectra within the blue portion of the spectrum.

Biologically active variants of naturally occurring luciferases may be used such as the Renilla luciferase variant RLuc8 (Leoning et al., 2006).

Alternative, non-luciferase, bioluminescent proteins that can be employed in the method described herein are any enzymes which can act on suitable substrates to generate a luminescent signal. Specific examples of such enzymes are β-galactosidase, lactamase, horseradish peroxidase, alkaline phophatase, β-glucuronidase and β-glucosidase. Synthetic luminescent substrates for these enzymes are well known in the art and are commercially available from companies, such as Tropix Inc. (Bedford, MA, USA). An example of a peroxidase is described by Hushpulian et al. (2007).

Preferably, the fluorescent or bioluminescent marker is in a form which is secreted from plant cells. If not inherently secreted when expressed in a plant cell, up to two modifications may need to be made to ensure secretion, namely the addition of an N-terminal signal sequence to target the protein into the endoplasmic reticulum (ER) and/or the addition of a signal, typically at the C-terminus, to ensure the protein is not retained in the ER.

N-terminal signal sequences are well known in the art and include, but are not limited to, viral envelope glycoprotein signal segments, Nicotiana nectarin signal peptide (U.S. Pat. No. 5,939,288), tobacco extensin signal, the soy oleosin oil body binding protein signal, Arabidopsis thaliana vacuolar basic chitinase signal peptide, and conglycinin secretory peptide.

With regard to ensuring the protein in not retained in the ER, each fluorescent or bioluminescent marker will have its own propensity to be secreted once in the ER. For example, GFP is retained in the cell. In cases where the marker is being retained in the ER the marker can be manipulated by standard techniques to ensure it is secreted, such as by adding 3 to 10, or about 4, glycines at the C-terminal end.

For instance, GFP is normally retained in plant cells, but was made secretable by the addition of the conglycinin secretory peptide at the N-terminus, and 4 glycines at the C-terminal end to ensure that the GFP was secreted to the apoplast (Nishizawa et al., 2003).

According to an example in which the selectable marker gene encodes a bioluminescent protein, a suitable substrate is required. The substrate can be provided to the plant tissue during one of the culture steps, but is at least required when the cells and/or tissues are being analysed to determine if the cells and/or tissues have been transformed.

The choice of the substrate can impact on the wavelength and the intensity of the light generated by the bioluminescent protein.

A widely known substrate is coelenterazine which occurs in cnidarians, copepods, chaetgnaths, ctenophores, decapod shrimps, mysid shrimps, radiolarians and some fish taxa (Greer and Szalay, 2002). For Renilla luciferase for example, coelenterazine analogues/derivatives are available that result in light emission between 418 and 512 nm (Inouye et al., 1997). A coelenterazine analogue/derivative (400A, DeepBlueC) has been described emitting light at 400 nm with Renilla luciferase (WO 01/46691). Other examples of coelenterazine analogues/derivatives are EnduRen and ViviRen.

Another class of Luciferin is a class of light-emitting biological pigments found in organisms capable of bioluminescence, which are oxidised in the presence of the enzyme luciferase to produce oxyluciferin and energy in the form of light. Luciferin, or 2-(6-hydroxybenzothiazol-2-yl)-2-thiazoline-4-carboxylic acid, was first isolated from the firefly *Photinus pyralis*. Since then, various forms of luciferin have been discovered and studied from various different organisms, mainly from the ocean, for example fish and squid, however, many have been identified in land dwelling organisms, for example, worms, beetles and various other insects (Day et al., 2004; Viviani, 2002).

There are at least five general types of luciferin, which are each chemically different and catalysed by chemically and structurally different luciferases that employ a wide range of different cofactors. First, is firefly luciferin, the substrate of firefly luciferase, which requires ATP for catalysis (EC 1.13.12.7). Second, is bacterial luciferin, also found in some squid and fish, that consists of a long chain aldehyde and a reduced riboflavin phosphate. Bacterial luciferase is FMNH-dependent. Third, is dinoflagellate luciferin, a tetrapyrrolic chlorophyll derivative found in dinoflagellates (marine plankton), the organisms responsible for night-time ocean phosphorescence. Dinoflagellate luciferase catalyses the oxidation of dinoflagellate luciferin and consists of three identical and catalytically active domains. Fourth, is the imidazolopyrazine vargulin, which is found in certain ostracods and deep-sea fish, for example, Porichthys. Last, is coelanterazine (an imidazolpyrazine), the light-emitter of the protein aequorin, found in radiolarians, ctenophores, cnidarians, squid, copepods, chaetognaths, fish and shrimp.

Examples of bacterial selectable markers are markers that confer antibiotic resistance such as ampicillin, erythromycin, chloramphenicol, tetracycline or kanamycin resistance. Exemplary selectable markers for selection of plant transformants include, but are not limited to, a hyg gene which encodes hygromycin resistance; a neomycin phosphotransferase (nptII) gene conferring resistance to kanamycin, paromomycin, G418; a glutathione-S-transferase gene from rat liver conferring resistance to glutathione derived herbicides as, for example, described in EP 256223; a glutamine synthetase gene conferring, upon overexpression, resistance to glutamine synthetase inhibitors such as phosphinothricin as, for example, described in WO 87/05327, an acetyltransferase gene from *Streptomyces viridochromogenes* conferring resistance to the selective agent phosphinothricin as, for example, described in EP 275957, a gene encoding a 5-enol-shikimate-3-phosphate synthase (EPSPS) conferring tolerance to N-phosphonomethylglycine as, for example, described by Hinchee et al. (1988), a bar gene conferring resistance against bialaphos as, for example, described in WO91/02071; a nitrilase gene such as bxn from *Klebsiella ozaenae* which confers resistance to bromoxynil (Stalker et al., 1988); a dihydrofolate reductase (DHFR) gene conferring resistance to methotrexate (Thillet et al., 1988); a mutant acetolactate synthase gene (ALS), which confers resistance to imidazolinone, sulfonylurea or other ALS-inhibiting chemicals (EP 154,204); a mutated anthranilate synthase gene that confers resistance to 5-methyl tryptophan; or a dalapon dehalogenase gene that confers resistance to the herbicide.

Examples of herbicide selectable markers are known in the art and described herein. Particular examples of herbicide selectable markers include those gene markers that confer herbicide resistance to glyphosate, glufosinate, or bialaphos.

Examples of selectable markers which confer a selective advantage to transformants in the presence of specific metabolites include trehalose-6-phophate synthase (At-TPS1) gene, β-glucoronidase (GUS) gene and phosphomannose isomerase (PMI) gene. In one example, a nucleic acid used in the method of the disclosure comprises the selectable marker gene encoding PMI, which confers the ability to metabolize mannose (U.S. Pat. Nos. 5,767,378 and 5,994,629, which are incorporated by reference herein). A plant cell transformed with a PMI gene may be selected by growing on media containing mannose only or mannose plus sucrose.

The one or more nucleic acids may be provided in one or more expression vector(s), together or separately. As used herein, an expression vector is a DNA vector that is capable of transforming a host cell and of effecting expression of one or more specified polynucleotide molecule(s). Preferred expression vectors for use in the method of the present disclosure can direct gene expression in plant cells, and particularly sorghum cells. Expression vectors useful for the in the method of the present disclosure contain regulatory sequences such as transcription control sequences, translation control sequences, origins of replication, and other regulatory sequences that are compatible with the sorghum tissue and that control the expression of the one or more nucleic acid introduced to the sorghum tissue. In particular, polynucleotides or vectors useful for the present invention include transcription control sequences. Transcription control sequences are sequences which control the initiation, elongation, and termination of transcription. Particularly important transcription control sequences are those which control transcription initiation, such as promoter and enhancer sequences. Suitable transcription control sequences include any transcription control sequence that can function in a transformed sorghum cell of the disclosure. Typically, the choice of regulatory sequences used depends on the target organism such as a plant and/or target organ or tissue of interest. Such regulatory sequences may be obtained from any eukaryotic organism such as plants or plant viruses, or may be chemically synthesized. A variety of such transcription control sequences for use in sorghum are known to those skilled in the art. Particularly preferred transcription control sequences are promoters active in directing transcription in plants, either constitutively or stage and/or tissue specific, depending on the use of the plant or parts thereof.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

As described herein, the method of producing a genetically-modified sorghum plant or regenerative part thereof comprises the step of culturing the DEC tissue(s) or sorghum tissue(s) into which one or more nucleic acids have been introduced on a medium, or a series of media, such that said culturing induces shoot formation from the DEC tissue(s), thereby producing one or more genetically modified shoot. Typically, regeneration of shoots from transformed plant explants comprises culturing the tissue explants on a series of culture media in a series of steps, wherein each media in the series comprises plant cell growth regulatory compounds in amounts sufficient to achieve the purpose of that step e.g., shoot inducement and elongation, shoot growth, and rooting. Accordingly, the method of the present disclosure contemplates culturing the tissue(s) into which one or more nucleic acids have been introduced on a series of media in order to produce one or more genetically modified shoot, including the production of shoots having roots.

In one example, at least one of the media in the series used to culture the tissue(s) and thereby produce genetically modified shoots may be a callus inducing medium (CIM) as described herein in the context of producing DEC tissue. For example, the CIM medium may be used to culture the tissue(s) during transformation of the tissue(s) and during a resting phase following introduction of the nucleic acid(s). In accordance with an embodiment of the method which comprises a selection for transformed tissue, a selection agent may be added to the CIM at the desired time. Alternatively, tissue(s) may be transferred to fresh CIM comprising the selection agent and cultured for a period sufficient to permit selection for transformed tissue(s) i.e., genetically modified tissue(s).

A particularly preferred example of a CIM which is useful for producing a genetically modified sorghum plant in a method of the disclosure is described in Table 6 of Example 4. Accordingly, the CIM which is useful for producing a genetically modified sorghum plant in a method of the disclosure can comprise the agent for reducing oxidative browning, the auxin and the cytokinin of the CIM as described in Table 6, optionally wherein any one of more of the agent for reducing oxidative browning, the auxin and the cytokinin are present at the same concentration as the CIM described in Table 6. The CIM which is useful for producing a genetically modified sorghum plant in a method of the disclosure can further comprise any one of more or all of the other constituents of the CIM described in Table 6, optionally at the same concentration as the CIM described in Table 6.

The series of media used to culture the tissue(s) in the method of the disclosure may also comprise a medium suitable for inducing the formation of shoot buds i.e., a shoot inducing media (SIM). Accordingly, the method of the disclosure may comprise transferring genetically modified tissue(s) from the CIM to SIM and culturing for a period of time sufficient to induce growth of shoot buds from the tissue(s). In one example, the SIM has a substantially similar formulation to the CIM described herein with the exception that the auxin and the cytokinin will be present in relative amounts sufficient to induce and/or stimulate growth of shoot buds from the transformed tissue(s). For example, the SIM may comprise a lower concentration of auxin and a higher concentration of cytokinin relative to that present in the CIM. In one example, the SIM may comprises BAP at a concentration of about 1.0 mg/L, 2,4-D at a concentration of about 0.5 mg/L and lipoic acid e.g., α-lipoic acid, at a concentration of about 1 mg/L. A particularly preferred example of a SIM which is useful for producing a genetically modified sorghum plant in a method of the disclosure is described in Table 6 of Example 4. Accordingly, the SIM which is useful for producing a genetically modified sorghum plant in a method of the disclosure can comprise the agent for reducing oxidative browning, the auxin and the cytokinin of the SIM as described in Table 6, optionally wherein any one of more of the agent for reducing oxidative browning, the auxin and the cytokinin are present at the same concentration as the SIM described in Table 6. The CIM which is useful for producing a genetically modified sorghum plant in a method of the disclosure can further comprise any one of more or all of the other constituents of the SIM described in Table 6, optionally at the same concentration as the SIM described in Table 6.

The series of media used to culture the tissue(s) in the method of the disclosure may also comprise a medium suitable for inducing the growth/regeneration of the shoots i.e., a shoot regeneration media (SRM). Accordingly, after a sufficient amount of time in the SIM, the method may comprise transferring genetically modified tissue(s) from the SIM to a SRM and culturing the tissues for a period of time sufficient to for elongation and growth of the shoots. This may involve excising the developing shoots from the tissue explants which were transformed and transferring the developing shoots to SRM for growth/elongation. In one example, the SRM has a formulation which is substantially similar to the SIM with the exception that auxin is absent or present in a very low amount relative to the amount of cytokinin in the medium. It may also be desirable for the SRM to comprise a higher concentration of cytokinin relative to the SIM to stimulate shoot growth and elongation. In one example, the SRM may comprises BAP at a concentration of about 1.0 mg/L, and lipoic acid e.g., α-lipoic acid, at a concentration of about 1 mg/L, and optionally a further cytokinin compound such as TDZ at a concentration of about 0.5 mg/L. A particularly preferred example of a SRM which is useful for producing a genetically modified sorghum plant in a method of the disclosure is described in Table 6 of Example 4. Accordingly, the SRM which is useful for producing a genetically modified sorghum plant in a method of the disclosure can comprise the agent for reducing oxidative browning and the cytokinin(s) of the SRM as described in Table 6, optionally wherein any one of more of the agent for reducing oxidative browning and the cytokinin are present at the same concentration as the SRM described in Table 6. The CRM which is useful for producing a genetically modified sorghum plant in a method of the disclosure can further comprise any one of more or all of the other constituents of the SRM described in Table 6, optionally at the same concentration as the SIM described in Table 6.

After a sufficient amount of time in SRM, the genetically modified shoots can be transferred to a rooting medium, described in the Examples herein as a root inducing medium (RIM), to induce root growth from the shoots. This may involve excising the developed shoots from tissue explants and transferring the developed shoots to RIM for root inducement and growth. Preferably, the rooting medium contains a root-inducing hormone, as are known in the art. Once the shoot has developed roots, it may be referred to as a plantlet.

The method may also comprise a further optional step of subjecting the genetically modified plantlets to environmental conditions sufficient to harden the plantlet. As used herein, the term "harden" or "hardening" or similar refers to the process of preparing the plantlet for normal environmental growth conditions e.g., such as in soil.

When the tissue(s) are cultured using a series of media, any one of more of the culture steps described herein may be repeated as necessary e.g., by replacing transferring the tissue(s) from the respective medium to a culture vessel comprising fresh media of the same type.

In accordance with any example in which the CIM is used to culture the tissue(s) in the method of the disclosure, the CIM may further comprise ascorbic acid and/or L-cysteine. For example, the CIM may comprise ascorbic acid. For example, the CIM may comprise L-cysteine. For example, the CIM may comprise ascorbic acid and L-cysteine. As demonstrated in Example 5 and Table 7 hereof, addition of ascorbic acid and/or L-cysteine to the CIM improved transformation efficiency.

Exemplary media for use in the production of genetically modified shoots in accordance with the method disclosed herein are provided in Table 6 in Example 4. In this regard, it is contemplated that the series of media used for producing a genetically modified sorghum plant in a method of the disclosure comprise one or more or all of the media described in Table 6 of Example 4. However, it will be appreciated by a person skilled in the art that certain constituents in those media can be varied without significantly altering the outcome of the method.

In each of the foregoing examples, the method of producing a genetically modified sorghum plant may comprise culturing the sorghum tissue(s) on one or more of the media in the series under dim light conditions, followed by culturing the sorghum tissue(s) on one or more further media in the series under light conditions having a greater intensity than the dim light conditions. For example, the method may comprise culturing the tissue(s) in CIM under dim light conditions, followed by culturing the tissue(s) in any one or more of the CIM, SIM and/or SRM described herein under light conditions having a greater intensity than the dim light conditions. The dim light conditions may have a light intensity of about 10 $\mu$mol $s^{-1}$ $m^{-2}$ to about 55 $\mu$mol $s^{-1}$ $m^{-2}$, or about 30 $\mu$mol $s^{-1}$ $m^{-2}$ to about 50 $\mu$mol $s^{-1}$ $m^{-2}$, or about 45 $\mu$mol $s^{-1}$ $m^{-2}$ to about 50 $\mu$mol $s^{-1}$ $m^{-2}$. In one preferred example, the dim light conditions comprise white light irradiated at an intensity of about 30 $\mu$mol $m^{-2}$ $sec^{-1}$ to about 45 $\mu$mol $m^{-2}$ $sec^{-1}$. The light conditions having a greater intensity than the dim light conditions may have a light intensity of about 55 $\mu$mol $s^{-1}$ $m^{-2}$ to about 90 $\mu$mol $s^{-1}$ $m^{-2}$, about 60 $\mu$mol $s^{-1}$ $m^{-2}$ to about 85 $\mu$mol $s^{-1}$ $m^{-2}$, or about 65 $\mu$mol $s^{-1}$ $m^{-2}$ to about 80 $\mu$mol $s^{-1}$ $m^{-2}$. In accordance with an example in which the dim light conditions comprise white light irradiated at an intensity of about 30 mol $m^{-2}$ $sec^{-1}$ to about 45 $\mu$mol $m^{-2}$ $sec^{-1}$, the subsequent culturing of the tissue(s) occurs under white light having an intensity of about 65 $\mu$mol $s^{-1}$ $m^{-2}$ to about 80 $\mu$mol $s^{-1}$ $m^{-2}$.

In each of the forgoing examples, it is contemplated that culturing of tissue(s) under the respective light conditions occurs with a photoperiod of about 12 h to about 20 hours, about 14 h to about 18 hours, or about 14 h to about 16 hours. For example, the culturing of tissue(s) under the respective light conditions may occur with a photoperiod of about 12 h, about 14 h, about 16 h, about 18 h, or about 20 h. In a preferred example, culturing of tissue(s) occurs with a photoperiod of about 14 h to about 16 hours e.g., 16 h.

In accordance with any example hereof, the culturing the sorghum tissue(s) on the medium, or on each medium in the series of media, occurs, independently, for about 1 week, about 2 weeks, about 3 weeks, about 4 weeks, about 5 weeks, or about 6 weeks. It will be appreciated by a skilled person that the length of culturing in the or each of the media may vary depending on the photoperiod and the length of the sorghum shoot to be achieved.

In one particular example, the culturing of tissue(s) at step (b) of the method of producing a genetically modified sorghum plant comprises:

(i) culturing the tissue(s) in CIM as described herein under dim light conditions comprising white light irradiated at an intensity of about 30 $\mu$mol $m^{-2}$ sec to about 45 $\mu$mol $m^{-2}$ $sec^{-1}$ with about 16 h photoperiod for about 3-5 weeks, optionally in the presence of a selection agent;

(ii) transferring the tissue(s) from (i) to SIM as described herein and culturing under light conditions comprising white light irradiated at an intensity of about 65 $\mu$mol $s^{-1}$ $m^{-2}$ to about 80 $\mu$mol $s^{-1}$ $m^{-2}$ with about 16 h photoperiod for about 2 weeks, optionally in the presence of a selection agent; and (iii) transferring the tissue(s) from (ii) to SRM as described herein and culturing under light conditions comprising white light irradiated at an intensity of about 65 $\mu$mol $s^{-1}$ $m^{-2}$ to about 80 $\mu$mol $s^{-1}$ $m^{-2}$ with about 16 h photoperiod for about 2 weeks, optionally in the presence of a selection agent; to thereby producing one or more genetically modified shoots.

In each of the forgoing examples, it is contemplated that the culturing of the tissue(s) occurs at a temperature, or at a series of temperature, suited for regeneration of sorghum explants to produce sorghum shoots. Appropriate temperature will be known to a person a skill in the art. For example, the culturing may be performed at a temperature of 24±2° C.

Additionally, the method of producing a genetically modified sorghum plant as described herein may comprise a further step of splitting the sorghum tissue(s), each into two or more parts, after introduction of the one or more nucleic acids. Preferably, splitting the sorghum tissue(s) occurs prior to shoot buds emerging from the tissue(s).

Processes for regeneration, development, and cultivation of plants from transformed explants are generally known in the art (Weissbach et al., In: Methods for Plant Molecular Biology, Academic Press, San Diego, Calif., (1988)). This regeneration and growth process typically includes the steps of selection of transformed cells or tissue, culturing those individualized cells or tissues through the usual stages of embryonic development, through to the rooted plantlet stage. The resulting genetically modified rooted shoots are thereafter planted in an appropriate plant growth medium such as soil.

The regenerated genetically modified sorghum plants may be self-pollinated to provide homozygous genetically modified sorghum plants. Otherwise, pollen obtained from the genetically modified sorghum plants may be crossed to seed-grown plants of agronomically important lines. Conversely, pollen from plants of these important lines is used to pollinate genetically modified sorghum plants produced using the method of the disclosure. A genetically modified plant produced by the method of the disclosure containing a desired nucleic acid (foreign or otherwise) may be cultivated using methods well known to one skilled in the art.

The inventors have shown that transforming DEC tissue of sorghum using a method of the disclosure achieves a transformation efficiency of at least 35%, such as, for example, a transformation efficiency of at least 40%, a transformation efficiency of at least 45%, a transformation efficiency of at least 50%, a transformation efficiency of at least 55%, a transformation efficiency of at least 60%, a transformation efficiency of at least 65%, a transformation efficiency of at least 70%, a transformation efficiency of at least 75%, a transformation efficiency of at least 80%, a transformation efficiency of at least 85%, or a transformation efficiency of at least 90%. Thus, the inventors have shown that a genetically modified sorghum plant produced from DEC tissue using the method described herein can be obtained with a genetic modification efficiency of at least 35%, such as, for example, a transformation efficiency of at least 40%, a transformation efficiency of at least 45%, a transformation efficiency of at least 50%, a transformation efficiency of at least 55%, a transformation efficiency of at least 60%, a transformation efficiency of at least 65%, a transformation efficiency of at least 70%, a transformation efficiency of at least 75%, a transformation efficiency of at least 80%, a transformation efficiency of at least 85%, or a transformation efficiency of at least 90%, wherein the genetic modification efficiency is expressed as the number of genetically modified shoots produced in step (b) of the method as a percentage of the number of DEC tissues used in step (a).

Accordingly, in one example, the method of the disclosure comprises the production of a genetically modified sorghum plant in which a genetic modification efficiency of at least 35% or at least 40% is obtained. As used herein, the term "genetic modification efficiency" refers to the number of genetically modified shoots produced from sorghum tissues into which a nucleic acid has been introduced using a method of the disclosure, expressed as a percentage of the number of tissues into which the nucleic acid was introduced e.g., during transformation.

One can determine the efficiency of transformation (and genetic modification efficiency) using any method known in the art. For example, genetic modification efficiency may be determined by detecting the presence of one or more of the nucleic acid introduced to the sorghum tissue using a method of the disclosure. In one example, a polymerase chain reaction (PCR) amplification or Southern blot analysis can be performed using methods known to those skilled in the art. Expression products of one or more of the nucleic acids introduced to the sorghum tissue can be detected in any of a variety of ways, depending upon the nature of the product, and include Western blot and enzyme assay. Transformation can also be detected by direct sequencing and/or hybridization protocols well known in the art. One particularly useful way to quantitate protein expression and to detect replication in different plant tissues is to use a reporter gene, such as GUS. In one example, transformation efficiency is determined by calculating the number of fluorescent or bioluminescent marker foci per tissue. Once genetically modified plants have been obtained, they may be grown to produce plant tissues or parts having the desired phenotype. Each of the foregoing methods are contemplated for use herein to identify genetically modified sorghum tissues or plants, as well as for determining efficiency of transformation (and genetic modification efficiency) using the method and DEC tissue of the disclosure. Such methods may also be useful in determining whether transformation of a nucleic acid is transient or stable.

The disclosure also provides a method of producing progeny of a genetically-modified sorghum plant, the method comprising selfing or crossing a genetically modified sorghum plant produced using the method described herein, to thereby produce progeny plants.

As used herein, the term "selfing", "self-fertilization" "self-pollination" or variations thereof means the fusion of male and female gametes from the same individual. Accordingly, in the context of the present disclosure, selfing refers to fusion of male and female gametes from a genetically modified sorghum plant produced by the method described herein.

As used herein, the term "crossing", "cross-pollination" or variations thereof means a cross between two different plants. Accordingly, in the context of the present disclosure, crossing refers to crossing a genetically modified sorghum plant produced by the method described herein with another sorghum plant.

As used herein, the term "progeny" or "progeny plants" or similar includes the descendants of a genetically modified sorghum plant produced using the method of the disclosure. The term "progeny" is intended to encompass "direct progeny" and "indirect progeny". As used herein, the term "direct progeny" refers to sorghum plants that derive from the seed (or, sometimes, other tissue) of a genetically modified sorghum plant produced by the method of the disclosure and is in the immediately subsequent generation. For instance, for a given lineage, a T2 plant is the direct progeny of a T1 plant. As used herein, the "indirect progeny" refers to sorghum plants that derive from the seed (or other tissue) of the direct progeny of a genetically modified sorghum plant produced by the method of the disclosure, or from the seed (or other tissue) of subsequent generations in that lineage; for instance, a T3 plant is the indirect progeny of a T1 plant.

In one example, the method of producing progeny of a genetically-modified sorghum plant further comprises the steps of:
(i) screening the progeny plants for the presence of the genetic modification or a phenotype conferred by the genetic modification; and
(ii) selecting progeny plants comprising the genetic modification and/or which display a phenotype conferred by the genetic modification, to thereby produce the one or more genetically modified sorghum plant(s).

Genetically Modified Sorghum

The disclosure also provides a genetically modified sorghum plant or part thereof produced by the method described herein. The term "plant" as used herein as a noun refers to whole plants, but as used as an adjective refers to any substance which is present in, obtained from, derived from, or related to a plant, such as for example, plant organs (e.g. leaves, stems, roots, flowers), single cells (e.g. pollen), seeds, plant cells and the like. The term "plant part" refers to all plant parts that comprise the plant DNA, including vegetative structures such as, for example, leaves or stems, roots, floral organs or structures, pollen, seed, seed parts such as an embryo, endosperm, scutellum or seed coat, plant tissue such as, for example, vascular tissue, cells and progeny of the same, as long as the plant part comprises a genetic modification which is introduced by the method of the disclosure.

The terms "seed" and "grain" are used interchangeably herein. "Grain" refers to mature grain such as harvested grain or grain which is still on a plant but ready for harvesting, but can also refer to grain after imbibition or germination, according to the context. Mature grain or seed commonly has a moisture content of less than about 18-20%. "Developing seed" as used herein refers to a seed prior to maturity, typically found in the reproductive structures of the plant after fertilisation or anthesis, but can also refer to such seeds prior to maturity which are isolated from a plant.

In a preferred example, the genetically modified sorghum plant is homozygous for each and every nucleic acid that has been introduced so that its progeny do not segregate for the desired phenotype. The genetically modified sorghum plant may also be heterozygous for the introduced nucleic acid(s), preferably uniformly heterozygous for the introduced nucleic acid(s), such as for example in F1 progeny which have been grown from hybrid seed. Such plants may provide advantages such as hybrid vigour, well known in the art.

In one example, the genetically modified sorghum plants of the disclosure are grown in the field, preferably as a population of at least 1,000 or 1,000,000 plants that are essentially the same, or in an area of at least 1 hectare. Planting densities differ according to the plant species, plant variety, climate, soil conditions, fertiliser rates and other factors as known in the art. Plants are harvested as is known in the art, which may comprise swathing, windrowing and/or reaping of plants, followed by threshing and/or winnowing of the plant material to separate the seed from the remainder of the plant parts often in the form of chaff. Alternatively, seed may be harvested from genetically modified sorghum plants in the field in a single process, namely combining.

Differentiating Embryogenic Callus (DEC) Tissue

Also provided is a DEC tissue of sorghum capable of being genetically modified with an efficiency of at least 35%. In one example, the DEC tissue is capable of being genetically modified with an efficiency of at least 40%. In one example, the DEC tissue is capable of being genetically modified with an efficiency of at least 45%. In one example, the DEC tissue is capable of being genetically modified with an efficiency of at least 50%. In one example, the DEC tissue is capable of being genetically modified with an efficiency of at least 55%. In one example, the DEC tissue is capable of being genetically modified with an efficiency of at least 60%. In one example, the DEC tissue is capable of being genetically modified with an efficiency of at least 65%. In one example, the DEC tissue is capable of being genetically modified with an efficiency of at least 70%. In one example, the DEC tissue is capable of being genetically modified with an efficiency of at least 75%. In one example, the DEC tissue is capable of being genetically modified with an efficiency of at least 80%. In one example, the DEC tissue is capable of being genetically modified with an efficiency of at least 85%. In one example, the DEC tissue is capable of being genetically modified with an efficiency of at least 90%. The efficiency with which the DEC tissue is capable of being genetically modified is calculated as the number of genetically modified shoots produced from the DEC tissues into which a nucleic acid has been transformed, expressed as a percentage of the number of tissues into which the nucleic acid was introduced e.g., during transformation. Expressed another way, the DEC tissues are capable of being transformed with one or more nucleic acids with a transformation efficiency of at least about 35%, at least about 40%, at least about 45%, at least about 50%, at least about 55%, at least about 60%, at least about 65%, at least about 70%, at least about 75%, at least about 80%, at least about 85%, or at least about 90%. When determining the efficiency of transformation, the DEC tissues may be genetically modified using a method of the disclosure, after or during which the efficiency of transformation is determined.

Alternatively, or in addition, the DEC tissue may have been produced using a method of the disclosure.

Preferably, the DEC tissue is green tissue.

In one example, the DEC tissue may be is produced and/or provided in the culture media described herein i.e., a culture media described for use in a method of producing DEC tissue.

Culture Medium

The present disclosure also provides a culture media which is suitable for preparing differentiating embryogenic callus (DEC) tissue of sorghum. A callus inducing medium (CIM) has already been described in the context of a method of producing DEC tissues, and the features of that CIM shall be taken to apply mutatis mutandis to each of the following examples of a culture media described, unless specifically stated otherwise.

In one example, the culture medium suitable for use in preparing DEC tissue of sorghum comprises a basal medium suitable for culturing plant cells supplemented with one or more auxins, one or more cytokinins and one or more agents which reduce oxidative browning, wherein the one or more agents which reduce oxidative browning are present in the medium at a concentration sufficient to prevent or reduce oxidative browning of the sorghum tissue; and wherein the one or more auxins and the one or more cytokinins are present in the medium in amounts relative to one another sufficient to produce DECs from the IEs during culture.

In one example, the one or more agents which reduce oxidative browning are selected from the group consisting of lipoic acid, melatonin, 2-aminoidan-2-phosphonic acid, ascorbic acid, alpha-tocopherol, 3,5-dibutyl-4-hydroxytoluene (BHT), cysteine, selenite, polyvinylpolypyrrolidone (PVPP), dithiothreitol (DTT), phenoxane, silver nitrate, citrate, glutathione, phytic acid, nordihydroguaiaretic acid (NDGA), and activated charcoal. Alternatively, or in addition, the one or more agents which reduce oxidative browning are present at a concentration of about 0.1 mg/L to about 10 mg/L, about 0.5 g/L to about 5 g/L, about 1 g/L to about 5 g/L, or about 1 g/L.

In one example, the one or more auxins are selected from the group consisting of indole-3-acetic acid (IAA), 4-chloroindole-3-acetic acid, phenylacetic acid, indole-3-butyric acid (IBA), 1-naphthaleneacetic acid (NAA), 2-naphthoxyacetic acid, 4-chlorophenoxyacetic acid, 2,4-dichlorophenoxyacetic acid (2,4-D), 2,4,5-Trichlorophenoxyacetic acid, 2,3,5-Triiodobenzoic acid, picloram, and salt forms of any one thereof. Alternatively, or in addition, the one or more auxins are present at a concentration of about 0.1 mg/L to about 5 mg/L, about 0.1 mg/L to about 3 mg/L, about 0.3 mg/L to about 2 mg/L, about 0.5 mg/L to about 1 mg/L or about 1 mg/L.

In one example, the one or more cytokinins are selected from the group consisting of benzylaminopurine (BAP), zeatin, kinetin, 2IP, zeatin riboside, diphenylurea and thidiazuron (TDZ). Alternatively, or in addition, the one or more cytokinins are present at a concentration of about 0.01 mg/L to about 2 mg/L, about 0.1 mg/L to about 2 mg/L, about 0.5 mg/L to about 2 mg/L, about 0.5 mg/L to about 1 mg/L, or about 0.5 mg/L.

In one example, culture medium is formulated to comprise auxin and cytokinin in relative amounts sufficient to induce and stimulate growth of nodular structures of differentiating cells which maintain embryogenic and organogenic potential, but without allowing substantial differentiation of the sorghum tissue into organized structures. In one example, the one or more auxins and the one or more cytokinins are present in medium at a weight ratio (auxin: cytokinin) of about 1.25:1, about 1.5:1, about 1.75:1, about 2:1, about 2.25:1, about 2.5:1, about 2.75:1, or about 3:1.

In a preferred example, wherein the agent which reduces oxidative browning is lipoic acid e.g., α-lipoic acid. For example, the lipoic acid may be present in the medium at a concentration of about 0.5 mg/L to about 2.0 mg/L, or about 1 mg/L.

The culture medium which is suitable for producing DEC tissue of sorghum may further comprise one or more other constituents which are known to be useful in plant tissue culture, including sources of macronutrients, micronutrients, vitamins, amino acids or nitrogen supplements, source(s) of carbon, undefined organic supplements, and solidifying agents. In one example, the culture medium comprises (in addition to an auxin, cytokinin and agent for reducing oxidative browning), peptone, a source of copper, an osmotic agent and/or a solidifying agent.

For example, peptone may be a included in the culture medium as source of nitrogen, vitamins and/or amino acids. In one example, the culture medium comprises peptone at a concentration of about 0.2 g/L to about 2 g/L, about 0.5 g/L to about 1.5 g/L, about 0.7 g/L to about 1 g/L, or about 0.8 g/L. In one example, peptone is present in the culture medium at a concentration of about 0.8 g/L.

The culture medium of the disclosure may also comprise a source of copper. For example, the culture medium may comprise cupric sulfate, copper chloride, copper nitrate, copper gluconate, or copper acetate. The copper may be present in culture medium at a concentration of about 0.1 mg/L to about 5 mg/L, about 0.3 mg/L to about 3 mg/L, about 0.5 mg/L to about 1.5 mg/L, about 0.7 mg/L to about 1 mg/L, or about 0.8 mg/L.

The culture medium described herein may comprise an osmotic agent. Suitable osmotic agents for use in plant cell culture are known in the art and contemplated for use in the culture medium described herein. For example, an osmotic for inclusion in the culture medium of the disclosure may be selected from myo-inositol, sucrose, mannitol, glycerol, sorbitol and maltose.

Solidifying agents useful in plant cell culture medium are known in the art e.g., agar, and are also contemplated inclusion in the culture medium of the disclosure.

In one example, the basal media is MS media.

An exemplary culture medium suitable for use in producing DEC tissue of sorghum comprises MS media at a concentration of about 4 g/L to about 5 g/L, 2,4-D at a concentration of about 1 mg/L, BAP at a concentration of about 0.5 mg/L and lipoic acid at a concentration of about 1 mg/L. In addition, the culture media may comprise one or more or all of L-proline at a concentration of about 0.5 g/L to about 1 g/L, peptone at a concentration of about 0.5 g/L to about 1 g/L, myo-inositol at a concentration of about 100 mg/L to about 200 mg/L, copper sulfate at a concentration of about 0.5 g/L to about 1 g/L, maltose at a concentration of about 10 g/L to about 50 g/L, and agar at a concentration of about 6 g/L to about 12 g/L.

The culture medium will preferably have a pH which is suitable for producing DEC tissue. For example, the culture media may have a pH of about pH 5.0 to about pH 6.0.

A particularly preferred example of culture medium which is useful for producing DEC tissue is described in Table 1 of Example 1 and is contemplated herein.

The culture medium as described in any example hereof, when used to prepare DEC tissue of sorghum e.g., in a method described herein.

EXAMPLES

Example 1. Preparation of DEC Tissue for *Sorghum bicolor* L

Plant Material

Plants of the grain sorghum of the inbred cultivar TX-430 (Miller 1984) were grown in a plant growth chamber (Conviron, PGC-20 flex) at 28±1° C. "day" temperature and 20±1° C. "night" temperature, with a. 16 hr photoperiod at a light intensity during the "day" of 900-1000 LUX. Panicles were covered with white translucent paper bags before flowering. Immature embryos were harvested from panicles 12-15 days after anthesis. Panicles were washed several times with water and developing seeds that were uniform in size were isolated and surface-sterilized using 20% commercial bleach mixed with 0.1% Tween-20 for 15-20 min. They were then washed with sterile distilled water 3 times each for 20 min, and blotted dry in a laminar flow hood. Immature embryos (IEs) ranging from 1.4 to 2.5 mm in length were aseptically isolated in the laminar flow hood and used as the starting tissue for preparation of green regenerative tissue.

Base Cultivation Media

Media used in the present study were based on MS (Murashige and Skoog, 1962), supplied by PhytoTechnology Laboratories (M519). The pH of the media was adjusted to 5.8 before sterilization at 121° C. for 15 min. Heat sensitive plant growth regulators and other additives such as copper sulfate ($CuSO_4$), lipoic acid, 1-cysteine, ascorbic acid, TDZ and Geneticin (G418, Sigma—used as a selection agent), were filter sterilized (0.2 μm) and added to the media after sterilization when the media had cooled to about 55° C. Media used in different steps of transformation and plant regeneration were summarized in Table 1.

Cultivation Methods and Materials

The isolated IEs ranging from 1.4 to 2.5 mm in length were placed onto callus induction media (CIM) of various compositions with their scutellum facing upward. CIM modified to improve callus quality and induction frequency from immature embryos, as well as callus regeneration media, included α-Lipoic acid (1 to 5 mg/l), Melatonin (5 to 10 mg/l) and 2-Aminoidan-2-phosphonic acid HCl (1 to 2 mg/l) unless otherwise stated. For the development of green tissue, immature embryos were incubated under fluorescent light of approximately 45-50 μmol $s^{-1}$ $m^{-2}$ (16 h/day) in a tissue culture room at 24±2° C. After three days of culture, the root and shoot poles of the immature embryos were aseptically separated and re-inoculated on to the same media (CIM) and maintained under the same conditions as described above. They were subcultured every two weeks for 6 weeks by chopping the callus into 2-3 mm portions, re-inoculating on to the same media (CIM) and maintaining under the same conditions described above, after which time the tissue cultures were evaluated for callus quality, callus induction efficiency and transformation efficiency. Callus induction frequency was calculated as the number of calli obtained (~5 mm) over total number of immature embryos inoculated, as a percentage.

Callus initiated from IEs in the first 3-4 weeks on CIM were mostly embryogenic and slowly differentiated in embryogenic callus with nodular structures which were coloured from pale to darker green. Embryogenic calli with green nodular structures were selected and maintained on the same medium (CIM) by subculturing every 2 weeks for up to 6 months or more, for use as explants for transformation. This type of tissue is termed herein as "differentiating embryogenic callus" tissue or "DEC" tissue, since this tissue forms nodular structures of differentiating cells which maintain embryogenic and organogenic potential, even though the tissues were really a mixture of callus cells, cells forming nodular structures and granular structures, and intermediate cells which the inventors understood were on the developmental pathway somewhere between callus (which is undifferentiated cells) and the 0.20 nodular structures. Sometimes, the tissues included early stage (globular) somatic embryos.

After six weeks on the CIM, some uniform green-coloured DEC tissue of about 4-7 mm diameter were transferred on to shoot induction medium (SIM) and cultured for another 2-3 weeks in order to begin organogenesis. Tissues which had induced shoot buds were then transferred to shoot regeneration medium (SRM) and again cultured for 2-3 weeks. Regenerability of DEC tissue of different ages (2-6 months from initiation) was also tested on SRM medium comprising different concentrations of BAP (0.5-1.0 mg/l) and TDZ (0.5-1.0 mg/l). The number of shoots were counted and the regeneration frequency (i.e. the number of shoots/ DEC tissue) was calculated after 3 weeks culture on SRM (total of approximately 5 weeks culture inclusive of culture on SIM and SRM). Individual shoots approximately 2-3 cm in length were transferred to shoot out growth (SOG) medium and cultured for another 2-3 weeks. Well-developed shoots (4-5 cm in length), were carefully separated from the cluster and transferred to root induction medium (RIM) and cultured for 3-4 weeks. For shoot induction to complete plant regeneration, 50-60 µmol s$^{-1}$ m$^{-2}$ (16 h/day) fluorescent light was used in the tissue culture room at 24±2° C. Shoots (about 8 cm in length) with numerous (often 15-20) healthy looking roots were transferred to soil and grown to maturity in a PC2 glasshouse at 28±11° C. The optimized culture medium composition for the different stages of plant transformation from callus induction to plant regeneration from green tissue induced from immature embryos is presented in Table 1.

TABLE 1

Medium used in DEC tissue induction and plant regeneration of sorghum

| Medium Name | Composition |
|---|---|
| CIM-callus induction medium | MS medium powder with vitamins (Phytotech labs, M519), 4.33 g/l; 2,4-Dichlorophenoxyacetic acid (2,4-D, Sigma D7299), 1 mg/l; Benzylaminopurine (BAP, Sigma, B3408), 0.5 mg/l; L-proline (Sigma, P5607), 0.7 g/l; α-Lipoic acid (LA, Sigma T1395), 1 mg/l; peptone (Merck 7284), 0.82 g/l; Myo-inositol (Sigma L5125), 150 mg/l; Copper sulfate (Rhone Poulene CL 942), 0.8 mg/l; Maltose (Sigma M9171), 30 g/l; Agar (Sigma A7291), 9 g/l, pH 5.8 |
| SIM-shoot induction medium | MS medium powder with vitamins, 4.33 g/l; 2,4-D, 0.5 mg/l; BAP, 1.0 mg/l; L-proline, 0.7 g/l; α-Lipoic acid, 1 mg/l; peptone, 0.82 g/l; Myo-inositol, 150 mg/l; Copper sulfate, 0.8 mg/l; Maltose, 30 g/l; Agar, 9 g/l, pH 5.8 |
| SRM-shoot regeneration medium | MS medium powder with vitamins, 4.33 g/l; BAP, 1.0 mg/l; TDZ, 0.5 mg/l; L-proline, 0.7 g/l; α-Lipoic acid, 1 mg/l; peptone, 0.82 g/l; Myo-inositol, 150 mg/l; Copper sulfate, 0.8 mg/l; Maltose, 30 g/l; Agar, 9 g/l, pH 5.8 |
| SOG-shoot out growth medium | MS medium powder with vitamins, 2.2 g/l; L-proline, 0.7 g/l; α-Lipoic acid, 1 mg/l; peptone, 0.82 g/l; Myo-inositol, 150 mg/l; Copper sulfate, 0.8 mg/l; Sucrose, 15 g/l; Agar, 9 g/l, pH 5.8 |
| RIM-root induction medium | MS medium powder with vitamins, 4.33 g/l; L-proline, 0.7 g/l; α-Lipoic acid, 1 mg/l; peptone, 0.82 g/l; Myo-inositol, 150 mg/l; Copper sulfate, 0.8 mg/l; sucrose, 15 g/l; Indole-3-acetic acid (IAA, Sigma 12886), 1 mg/l; Indole-3-butyric acid (IBA), 1 mg/l; Naphthaleneacetic acid (NAA, Sigma N0640), 1 mg/l; Polyvinylpyrrolidone (40,000 MW, Sigma PVP-40), 2 g/l; Agar 9 g/l, pH 5.8 |

Example 2. Effect of α-Lipoic Acid on DEC Tissue Induction Frequency and Quality Sets of IEs ranging from 1.4 to 2.5 mm in length, each set isolated from one panicle, were aseptically isolated and cultured on CIM medium as described in Example 1. Some sets were cultured with the addition of α-Lipoic acid (LA, 1 mg/l or 5 mg/), others without, in order to determine the effect of this agent.

After 6 weeks of culture including subculture every two weeks onto the same medium, DEC tissue induction frequency and quality were evaluated. The data are presented in Table 2. Small immature embryos (1.5-2 mm) cultured on CIM with LA had greater DEC tissue induction frequency (significant at p<0.01) with improved quality of nodular structures compared to CIM without LA, which tended to be white or pale yellow with granular callus and fewer nodular structures. In this context, improved quality refers to the visual appearance of the nodular structures, their colour being pale green to darker green rather than tending to brown, indicating improved health and also the relative amount of tissue that had started to develop somatic embryos of about 50% globular stage tissue. A similar trend of improvement was observed for larger immature embryos (>2 mm) as starting material when cultured in the presence of LA, but this was not statistically significant (p=0.1). Callus from Immature embryos (1.4-2 mm or >2 mm) cultured without LA tended to be white/pale yellow to green with less nodular structures and also less globular stage embryos compared to CIM with LA (Table 2). There was no significant further improvement observed using the higher concentration of LA (5 mg/l) compared to 1 mg/ml.

TABLE 2

Comparison of DEC tissue induction frequency and quality with and without LA in induction medium

| Immature embryo size | Parameter | Medium | |
|---|---|---|---|
| | | CIM + 0 mg/l LA | CIM + 1 mg/l LA |
| 1.5-2 mm | Green tissue induction frequency* | 61.3 ± 3.21 | 79.0 ± 6.5 |
| | DEC tissue quality | Average quality | High quality |
| >2 mm | Green tissue induction frequency** | 52.3 ± 3.05 | 59.0 ± 5.5 |
| | DEC tissue quality | Low quality | Good quality |

Values are the means with the ± reported as standard deviation (SD).
*Significant at p < 0.013.
**Not significant.

Example 3. Effect of α-Lipoic Acid on DEC Tissue Yield

Forty five IEs ranging from 1.4 to 2.5 mm in length (three replicas of 15 each), were aseptically isolated and cultured onto CIM medium with and without the addition of LA (1 mg/ml) as described above in Example 2.

After 4 to 12 weeks of culture, the number of DEC tissues obtained were counted. The data are presented in Table 3. The number of DEC tissue pieces (~5 mm) obtained at 12 weeks on CIM with LA was almost double when compared to using CIM without LA. Furthermore, the quality of the DEC tissues obtained on CIM with LA was improved compared to using the medium without LA.

TABLE 3

Effect of LA on DEC tissue yield of sorghum

| Culturing time | DEC yield in number ~5 mm each | |
|---|---|---|
| (weeks) | CIM + 1 mg/l LA | CIM without LA |
| 4 | 36 | 29 |
| 6 | 90 | 45 |
| 8 | 120 | 45 |
| 10 | 218 | 150 |
| 12 | 825 | 435 |

Example 4. Effect of α-Lipoic Acid on Regeneration Efficiency and Number of Shoots/DEC Tissue Uniform ready-to-use high quality green DEC tissues (5 mm) each with nodular structures induced on CIM medium with or without added LA were transferred to shoot induction medium (SIM) with and without LA and cultured for another 2-3 weeks. Tissues with induced shoot buds were then transferred to shoot regeneration medium (SRM) with or without added LA and again cultured for 2 weeks. Regenerability of green tissues of different ages (2-6 months from initiation) was tested on SRM medium containing different concentrations of BAP (0.5-1.0 mg/l) and TDZ (0.5-1.0 mg/l). Tissues including the shoot buds were again cultured on hormone free medium (SOG) with or without LA. The number of shoots was counted after 2 weeks of culture on SRM and the regeneration frequency (number of shoots/DEC tissue) calculated.

Use of the shoot regeneration medium with the combination of BAP and TDZ was superior compared with use of BAP only. The regeneration frequency and the number of shoots/DEC tissue for different ages of DEC tissue is presented in Table 4. Without LA in the SIM and SRM media, the regeneration frequency and number of shoots/DEC tissue slowly declined as the tissues aged. However, when LA was included in both media, the regeneration frequency and number of shoots/DEC tissue did not decline as much for the different ages of DEC tissue. Generation of DEC tissue and plant regeneration from immature embryos of Sorghum, cultured with and without LA in SIM and SRM, is shown in FIG. 1.

TABLE 4

Effect of lipoic acid on regeneration frequency

| DEC tissue age in months (from immature embryo isolation) | Regeneration frequency (%) | | Number of shoots/callus | |
|---|---|---|---|---|
| | No LA in SIM and SRM | LA in SIM and SRM | No LA in SIM and SRM | LA in SIM and SRM |
| 2 | 92.3 ± 3.05 | 97.6 ± 2.5 | 22 ± 3.6$^a$ | 40 ± 4.5$^b$ |
| 4 | 86 ± 2.0* | 97 ± 2.6* | 16 ± 2.0$^c$ | 40 ± 1.5$^d$ |
| 6 | 81 ± 1.0** | 94.3 ± 2.0** | 14 ± 2.0$^e$ | 33 ± 2.5$^f$ |

Values are the means with the ± reported as standard deviation (SD). Different letters in the row, in calculation of number of shoots/calls is significant (P < 0.05).
*Significant at P = 0.004.
**Significant at P = <0.001.

Example 5. DNA Content of Regenerated Plantlets from Different Callus Lines

In this experiment, the relative DNA content of regenerated plantlets from different callus lines (5 months to 2 years) was determined using flow cytometry (FCM).

The variation in ploidy level between regenerated sorghum plants from different age DEC tissues (18 months, 12 months, 9 months, 6 months etc from time of induction from immature embryo) and WT (plant raised from seed) were determined using a Partec PAII flow cytometer. Young leaf tissues 50 mg from WT and regenerated plants were chopped into small pieces using a razor blade in a Petri dish in 1 ml of Galbraiths buffer (45 mM $MgCl_2$, 20 mM MOPS, 30 mM sodium citrate 0.1% (v/v) Triton X-100, pH adjusted to 7 using 1M NaOH). The homogenate for each sample was mixed several times using a pipette, after which the nuclei suspension was filtered through a 38 µM nylon cloth into 1.5 ml eppendorf tubes and centrifuged at 1000 rpm for 2.5 minutes. Around 800 µl of supernatant for each sample was removed leaving 200 µl of homogenate, to which 10 µl propidium iodide solution (1 mg/ml, Sigma) was added. The homogenate containing propidium iodide was transferred to flow cytometer tube, incubated at room temperature 1 hr and analysed.

WT seed was used as a control for the analyses to determine relative DNA content in 2 independently selected regenerates from different age callus lines. 2C DNA content was calculated based on the value of the fluorescence intensity of G1 peaks for both the internal standard and the sample. The ploidy level and DNA content of the unknown samples were calculated as follows:

Ploidy Nuclear DNA content=Mean position of sample peak/Mean position of standard peak× DNA content of the standard.

The nuclear 2C DNA content of sorghum is considered as 1.74 (Chae et al. 2013).

Figure 2:
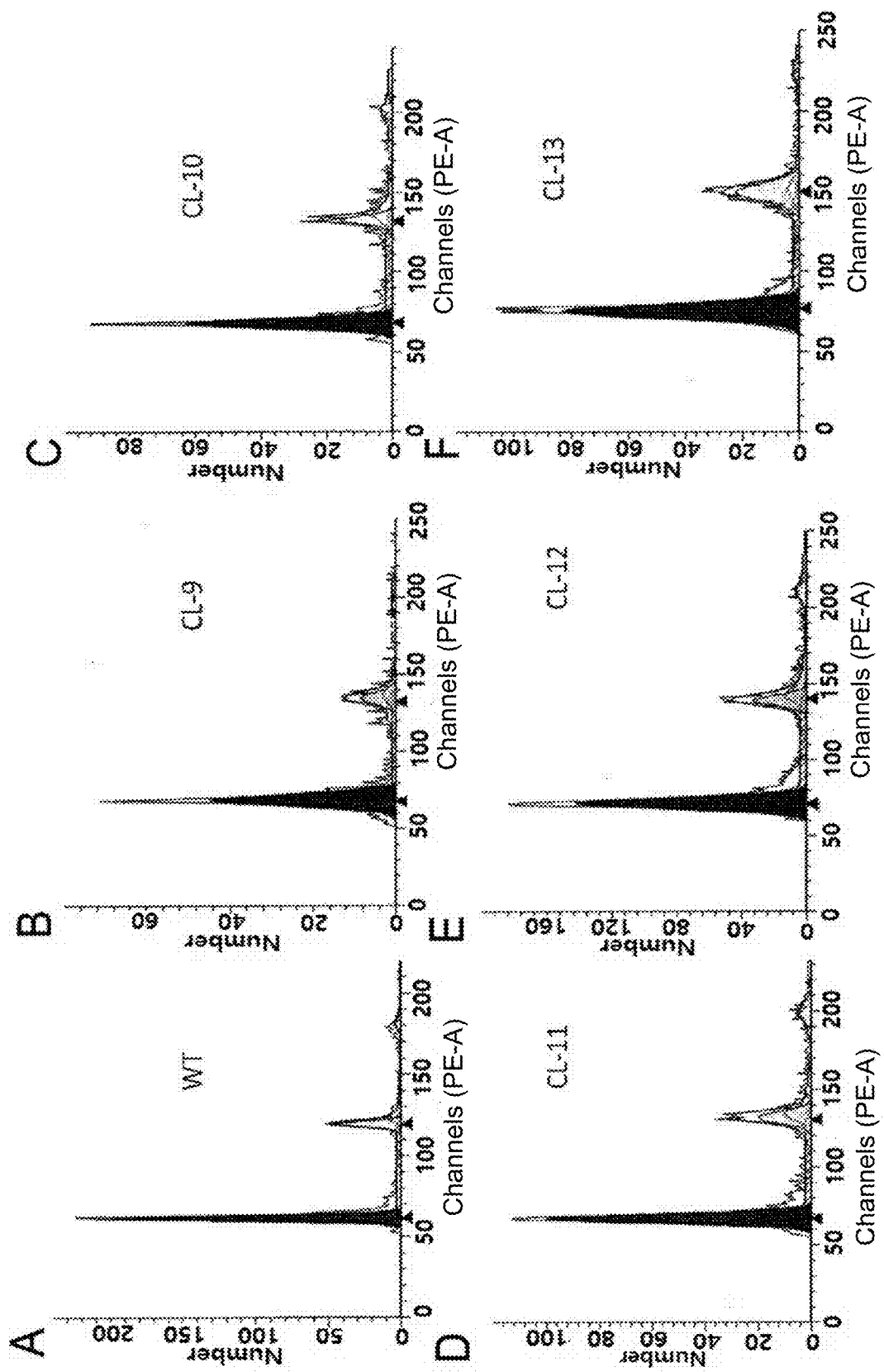
FIG. 2. Histograms of nuclei extracted from leaf tissue of regenerated plants from different age callus lines and WT seedling of Sorghum: (A) WT leaf tissue from 3 weeks old plant; (B) CL9: 24 months; (C) CL10: 12 months old; (D-E) CL-11 and CL12 6 months old; (F) CL13 5 months old DEC tissue.

FCM revealed that nearly all the plants were diploid and DNA content was comparable to WT seed (Table 5). The differences in DNA content between WT and regenerated lines was not statistically significant (p=0.19) by one-way ANOVA. G2/G1 ratio of WT and regenerated plants from different callus lines was less than 2.0 and there was no significant difference between this ratio in WT and regenerated plants. Histograms of relative nuclear DNA content of leaves from WT and regenerated plants from DEC tissues did not show any distinct G0/G1 peaks (FIG. 2).

It was concluded that the methods used to prepare DEC tissue did not negatively affect the tissues in their DNA content and therefore ploidy, unlike other sorghum tissue culture methods when maintained over 6 months or more. The DEC tissue method was therefore more likely to produce phenotypically normal transgenic sorghum plants and plant parts.

TABLE 5

2C values of nuclear DNA content of leaf tissue regenerated from different age callus lines.

| Number of the callus line | Age of the callus line from induction | nDNA content (pg) |
|---|---|---|
| CL-09 | 24 months | 1.72 ± 0.014$^a$ |
| CL-10 | 12 months | 1.71 ± 0.028$^a$ |
| CL-11 | 6 months | 1.78 ± 0.169$^a$ |
| CL-12 | 6 months | 1.76 ± 0.007$^a$ |
| CL-13 | 5 months | 1.98 ± 0.169$^a$ |
| WT Sorghum | | 1.67 pg $^a$ |

$^a$ Each treatment included 2 plants with 2 replications. Means were compared using the Multiple Pair wise Comparison Procedure and found to be not significantly different at p = 0.19.

Example 6. Geneticin as Selection Agent for Transformed Tissues

The experiments described in Examples 2-4 for culturing and regeneration conditions did not use a selective agent for transformed cells since no genetic construct was introduced into the cells. As a next step in developing the transformation method using regenerable DEC tissues/somatic embryos, the sensitivity of the DEC tissues/somatic embryos to Geneticin was determined.

The experiment was carried out using 6 weeks-old uniform, healthy green-coloured DEC tissues about 5 mm in size and which contained some somatic embryos, produced after culturing on CIM containing 1 mg/l LA. The Geneticin levels used were 0, 15, 25, 35 and 45 mg/L, respectively. Three replicates each of 15 green DEC tissue pieces per plate were used for each concentration of Geneticin tested.

The tissues were cultured for 6 weeks, being subcultured every two weeks onto the same medium, including the same Geneticin concentrations.

After 6 weeks of culture, the number of green DEC tissues that had survived was counted. The data are presented in Table 6.

DEC tissues (about 5 mm) began to display geneticin stress symptoms on selective callus induction media (CIM with geneticin) within 3 weeks of culture. DEC tissues without geneticin (G0) in media showed continued cell proliferation and healthy growth without any loss of calli. After 8 weeks on CIM media with different concentrations of geneticin (15, 25, and 45 mg/), DEC tissues showed differential growth responses. After 8 weeks on CIM with G25 and 35 mg/l, most of the calli turned dark brown in colour with no signs of survival. Very few calli (2-6) survived with dead patches. On this basis, geneticin at a final concentration of 25 mg/i was used in the callus induction media for 3 cycles (2 weeks each) and then increased to 30 mg/i for one cycle in shoot induction media (Table 6). Different concentrations of geneticin in CIM and SIM was deemed optimal in preventing shoot regeneration from non-transformed callus.

TABLE 6

Survival of DEC tissues/somatic embryos on medium containing Geneticin

| Base Medium | Geneticin concentration (mg/l) | Green DEC tissue survival (%) |
|---|---|---|
| CIM + 1 mg/l LA | 0 | 100 ± 0.0 |
| | 15 | 80 ± 1.0 |
| | 25 | 4 ± 2.6 |
| | 35 | 2 ± 0.5 |
| | 45 | 0 |

Example 7. Particle-Bombardment of Green Regenerative DEC Tissues

Figure 3:
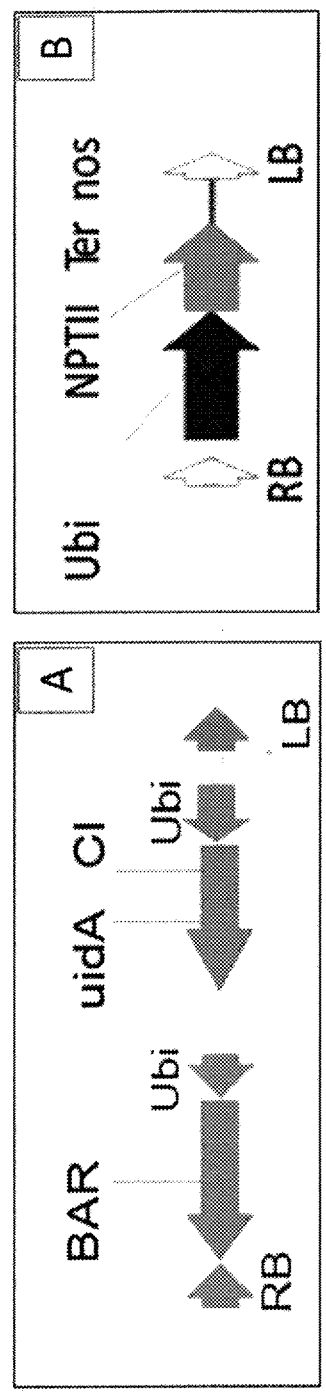
FIG. 3. Schematic representation of plasmids used for bombardment of sorghum DEC tissue. (A) pUbi-BAR; and (B) pBSV003.

A genetic vector was obtained which contained uidA (GUS) and bar genes designed for expression in plant cells. The idA gene was under the regulatory control of a maize polyubiquitin promoter (pUbi) and an *Agrobacterium tumefaciens* octopine synthase polyadenylation/terminator (ocs 3') sequence. The sequence between the promoter and the protein coding region included the 5' UTR and first intron of the Ubi gene. The uidA reporter gene also contained, within its protein coding region, an intron from a castor bean catalase gene which prevented translation of functional GUS protein in *Agrobacterium*, thereby reducing the background GUS gene expression in inoculated plant tissues. Therefore, any GUS expression would be due to expression of the uidA gene in the plant cells. The bar gene was also under the regulatory control of a pUbi promoter and terminated with an *Agrobacterium* nopaline synthase 3' regulatory sequence (nos 3') (Richardsom et al., 2014). The uidA/bar vector is schematically represented in FIG. 3A. The uidA/bar vector was initially used in experiments to detect transient gene expression in the sorghum DEC tissues.

Another binary plasmid (pBSV003), which contained a gene encoding the neomycin phosphotransferase II (NptII) providing resistance to the antibiotic Geneticin, under the control of the pUbi promoter and terminated by the nos 3' region (FIG. 3B), was also obtained for experiments to achieve stable transformation.

Plasmid DNAs were isolated using a Zymopure™ Maxiprep kit (USA) according to the manufacturer's instructions.

Uniform healthy, green regenerative DEC tissues (4-5 mm in size), produced using methods described in the foregoing examples and having been cultured for 6 weeks to 6 months from initiation, were used for microprojectile-mediated transformation (bombardment) with the plasmids. Approximately 15 uniform green DEC tissues (each 4-5 mm) were placed at the centre of a petri dish (15×90 mm diameter) containing CIM-osmotic medium (Table 7) and incubated in the dark for about 4 hrs prior to bombardment. Bombardment was performed with a PDS-1000 He device (Biorad, Hercules, Calif.) as described by Liu et al. (2014). Briefly, plasmid DNA (1 μg/μl) was precipitated onto 0.6 μm gold particles and accelerated with helium pressure using 1350 psi rupture discs at 26-27 Hg vacuum. Post bombardment, the DEC tissues were kept on the same osmotic medium overnight and transferred to pre-selection medium the next morning and incubated for another 3-4 days. Bombarded calli were incubated under fluorescent light of approximately 95-100 μmol $s^{-1}$ $m^{-2}$ (16 h/day) in the tissue culture room, which was set up at 24±1° C.

TABLE 7

Composition of medium used in transformation, selection and regeneration.

| Name of the medium | Composition | Culture duration |
|---|---|---|
| CIM-Osmotic Medium | MS medium powder with vitamins, 4.33 g/l; 2,4-D, 1 mg/l; BAP, 0.5 mg/l; L-proline, 0.7 g/l; L-Lipoic acid, 1 mg/l; peptone, 0.82 g/l; Myo-inositol, 150 mg/l; Copper sulfate, 0.8 mg/l; Manitol, 36.4 g/l; Sorbitol, 36.4 g/l; Agar, 8.5 g/l, pH 5.8 | 3-4 hrs before bombardment; o/n post bombardment |
| CIM-pre selection medium | MS medium powder with vitamins, 4.33 g/l; 2,4-D, 1 mg/l; BAP, 0.5 mg/l; L-proline, 0.7 g/l; L-Lipoic acid, 1 mg/l; peptone, 0.82 g/l; Myo-inositod 150 mg/l; Copper sulfate, 0.8 mg/l; Maltose, 30 g/l; L-cysteine, 50 mg/l; Ascorbic acid, 15 mg/l; Agar, 9 g/l, pH 5.8 | 3-4 days |
| CIM-callus induction medium/G25 | MS medium powder with vitamins, 4.33 g/l; 2,4-D, 1 mg/l; BAP, 0.5 mg/l; L-proline, 0.7 g/l; L-Lipoic acid, 1 mg/l; peptone, 0.82 g/l; Myo-inositol, 150 mg/l; Copper sulfate, 0.8 mg/l; Maltose, 30 g/l; Geneticin, 25 mg/l; Agar, 9 g/l, pH 5.8 | 4 weeks |
| SIM-shoot induction medium/G25 | MS medium powder with vitamins, 4.33 g/l; BAP, 1.0 mg/l; 2,4-D, 0.5 mg/l; L-proline, 0.7 g/l; L-Lipoic acid, 1 mg/l; peptone, 0.82 g/l; Myo-inositol, 150 mg/l; Copper sulfate, 0.8 mg/l; Maltose, 30 g/l; Geneticin, 25 mg/l; Agar, 9 g/l, pH 5.8 | 2 weeks |
| SRM-shoot regeneration medium/G25 | MS medium powder with vitamins, 4.33 g/l; BAP, 1.0 mg/l; TDZ, 0.5 mg/l; L-proline, 0.7 g/l; L-Lipoic acid, 1 mg/l; peptone, 0.82 g/l; Myo-inositol, 150 mg/l; Copper sulfate, 0.8 mg/l; Maltose, 30 g/l; Geneticin, 25 mg/l; Agar, 9 g/l, pH 5.8 | 2 weeks |
| SOG-shoot out growth medium/G30 | MS medium powder with vitamins, 2.2 g/l; L-proline, 0.7 g/l; L-Lipoic acid, 1 mg/l; peptone, 0.82 g/l; Myo-inositol, 150 mg/l; Copper sulfate, 0.8 mg/l; Sucrose, 15 g/l; Geneticin, 30 mg/l; Agar, 9 g/l, pH 5.8 | 2 weeks |
| RIM-root induction medium/G15 | MS medium powder with vitamins, 4.33 g/l; L-proline, 0.7 g/l; L-Lipoic acid, 1 mg/l; peptone, 0.82 g/l; Myo-inositol, 150 mg/l; Copper sulfate, 0.8 mg/l; sucrose, 15 g/l; IAA, 1 mg/l; IBA, 1 mg/l; NAA, 1 mg/l; PVP, 2 g/l; Geneticin, 15 mg/l; Agar 9 g/l, pH 5.8 | 4 weeks |

Figure 4:
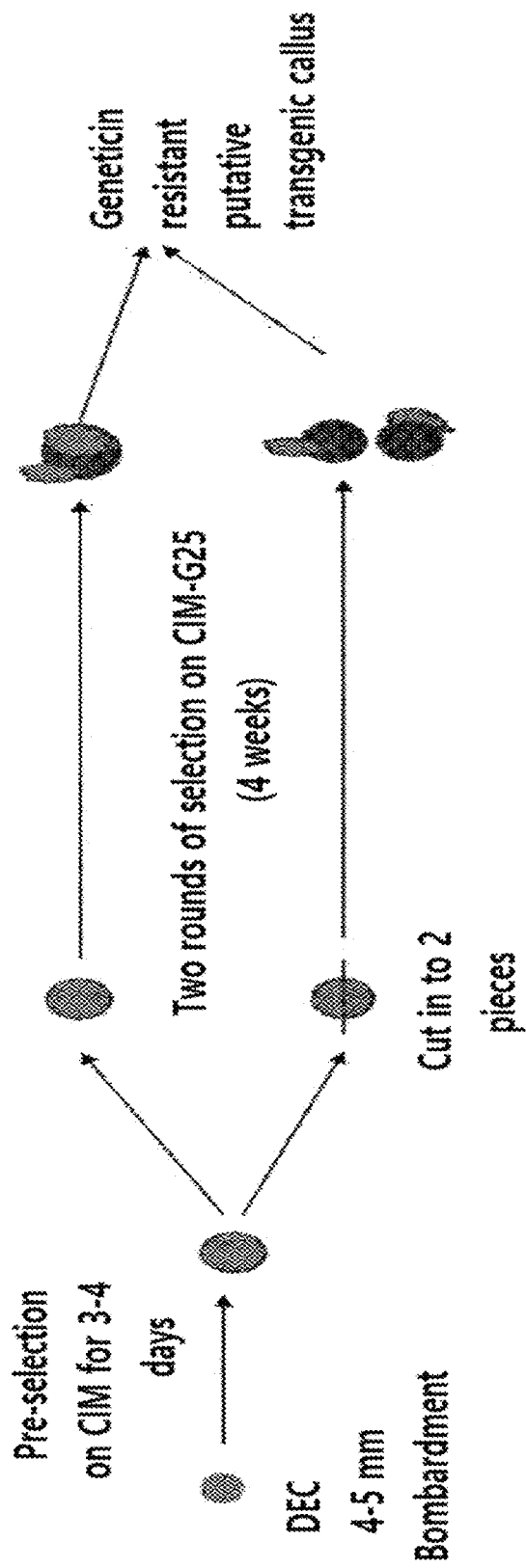
FIG. 4. Flow diagram illustrating method of cutting and culturing bombarded DEC tissue in selection media.

Example 8. Effect of L-Cysteine and Ascorbic Acid on Recovery of Post-Bombarded Tissues and Gene Expression Green DEC tissues bombarded with the genetic vector plasmid having a selectable marker encoding NptII (providing resistance to the antibiotic Geneticin) in Example 7 were transferred to CIM-PS medium (as per Table 7) for 3-4 days before any selection, with or without addition to the medium of two compounds as antioxidants, L-cysteine (50 mg/l) and ascorbic acid (15 mg/i). Without the addition of these antioxidants in pre-selection medium, many of the bombarded tissues turned brown, some quite dark brown in colour, and many lost any ability to grow further. After 3-4 days on pre-selection medium (with or without L-cysteine and ascorbic acid), the bombarded tissues were subjected to GUS staining and viewed under a microscope to count the distinctive blue (GUS positive) spots. Strong GUS gene expression was observed in all bombarded DEC-tissue with at least 15 foci/callus. The inclusion of the two antioxidants in the pre-selection medium further improved the efficiency of the transformation (at least 20 foci/callus) as shown by the transient expression of the GUS gene (Table 8). The average number of GUS foci observed in DEC tissue cultured on CIM with cysteine and ascorbic acid was around 27 GUS foci/callus, and the distinctive GUS positive spots were observed all over the tissues (5-7 mm) rather than clustered. In addition to this, multiple shoots were regenerated from a single DEC tissue, including from tissue selected with geneticin, prompting an assessment of modified selection procedures capable of obtaining multiple events from a single DEC explant. To explore this, some of the bombarded tissues were split into two approximately equal parts (as shown in FIG. 4) and cultured as described below in Example 9.

TABLE 8

Effect of L-cysteine and ascorbic acid post bombardment

| Number of tissues bombarded | Number of brown tissues | | Number of GUS spots/tissue | |
|---|---|---|---|---|
| | CIM no L-cysteine and ascorbic acid | CIM + L-cysteine and ascorbic acid | CIM no L-cysteine and ascorbic acid | CIM + cysteine and ascorbic acid |
| Exp-A: 75 | 15 | 8 | 12 | 25 |
| Exp-B: 75 | 18 | 11 | 13 | 20 |
| Exp-C: 75 | 23 | 14 | 7 | 38 |
| Average | 18.6 ± 4.04 | 11.0 ± 4.04 | 10.6 ± 3.2 | 27.6 ± 9.2 |

Values are the mean with the ± reported as a standard deviation.
*Not significant (p = 0.083);
**significant (p = 0.039).

Example 9. Selection and Regeneration of Transgenic Plants with Optimised Conditions Following bombardment and 3-4 days culture on pre-selection medium without selective agent (Geneticin), the bombarded tissues from Example 8 had increased in size from 4-5 mm to about 6-7 mm. These tissues were transferred to selective medium CIM/G25 containing 25 mg/l Geneticin, and cultured for a further 4 weeks (two cycles). Some of the tissues were split into two approximately equal pieces whereas others were not, in an attempt to see if more transformants could be obtained per tissue (FIG. 4). All of the tissues were cultured on the media as described in Table 7 and maintained in order to regenerate putative transgenic plants.

Figure 6:
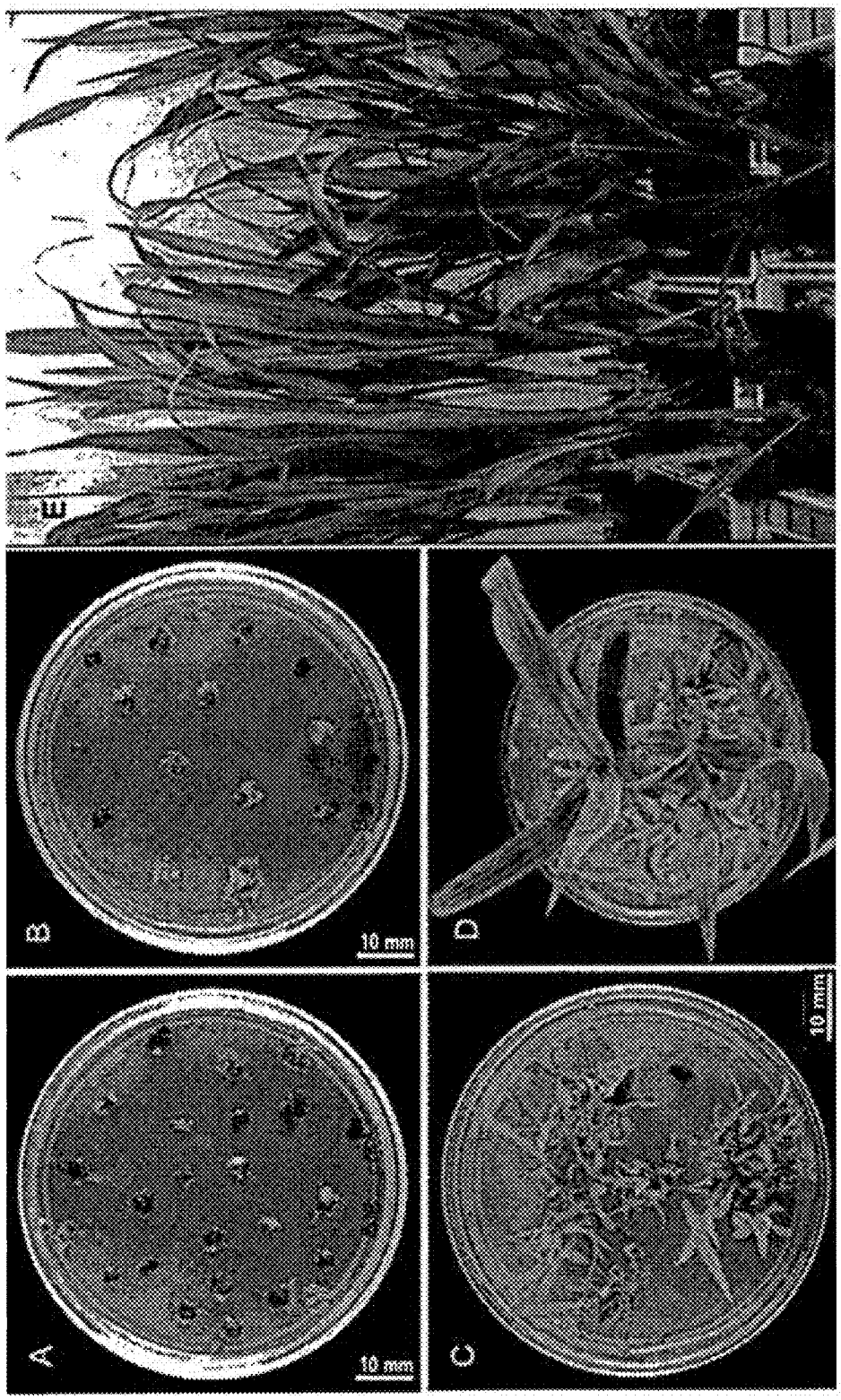
FIG. 6. Selection and regeneration of transgenic sorghum plants: (A) Non-transformed (control) calli on CIM+G25; (B) Transformed calli on CIM+G25; (C-D) Shoot regeneration from transformed callus; and (E) PCR confirmed transgenic plants in plant growth chamber.

Plants were regenerated efficiently upon growth on these media. Each bombarded tissue and the shoots obtained from it were subcultured and maintained separately for calculation of the transformation efficiency for the respective groups. Positive transformation was confirmed by PCR on plant genomic DNA isolated from shoot samples, showing the presence of the selectable marker gene. The selection and transformation of transgenic sorghum is illustrated in FIG. 6. The number of transformants was calculated per input DEC tissue. That is, transformation efficiency (TE %) was calculated as number of independent events regenerated/total number of explants bombarded×100. The data for transformation efficiency is presented in Table 9.

Although more shoots (>5) were obtained from a single selected split callus, all shoots were considered to be clones of the same callus. The average transformation efficiency obtained from split tissues for a single construct bombarded was around 46%, which can be compared with transformation efficiency of 27% for non-split tissues. The transformation efficiency obtained when splitting the bombarded tissue was more than double the transformation efficiency previously reported by Liu and Godwin (2012) in TX430 using immature embryos.

The number of transgenic plants regenerated from the tissues which had been split in two was significantly increased compared to tissues that had not been split. This provided recovery of multiple shoots from a single bombarded tissue, due to the multiple foci of transformation.

TABLE 9

Transformation efficiency

| Number of DEC tissues originally bombarded | Method of subculture | Total number of independent transgenic events regenerated | Transformation efficiency (%) |
|---|---|---|---|
| 150 | Tissues split into two equal parts - 300 pieces | 140 | 46.6 |
| 180 | Tissues not split - 180 pieces | 49 | 27.2 |

Example 10. Molecular Analysis of T0 Transformants

DNA from 20 randomly selected putative transformants bombarded with pBSV003 in Example 7 were subjected to PCR analysis to confirm the presence of the NptII gene using NptII primers. All of the plants were morphologically normal, male and female fertile, and produced seed.

Genomic DNA was isolated from young leaves of putative transgenic shoots as described by Mieog et al. (2013) with minor modifications. Briefly, freeze dried leaf tissues (1 cm$^2$) were smashed in individual wells of 96 well plate with stainless steel ball bearings using a tissuelyser-II (Qiagen). 375 µl of DNA extraction buffer (0.1M Tris-HCl pH 8.0, 0.05 M EDTA pH 8.0, 1.25% SDS) was added to each of the smashed tissues. The mixtures were then incubated at 65° C. for 1 hr, after which 187 µl of 6 M ammonium acetate was added and the samples incubated at 4° C. for a further 30 min. The samples were then centrifuged at 3000 rpm for 30 min at room temperature. 340 µl of supernatant was recovered from each sample and transferred to a new 96-well plate containing 220 µl of isopropanol in each well for precipitation of the DNA. The DNAs were rinsed once with 70% ethanol, briefly dried and dissolved in 220 µl sterile distilled water and left overnight at 4° C. To confirm the presence of NptII gene, NPTII-F: 5'-ATGATTGAACAAGATGGATTG-3' (SEQ ID NO: 1) and NPTII-R: 5'-GCTATGTCCTGA-TAGCGGTCC-3' (SEQ ID NO: 2) primers were used and PCR analysis was performed on genomic DNA of putative transgenic shoots. The thermal cycle profile for the PCR was: initial denaturation at 94° C. for 15 min, 35 cycles of 94° C. for 60 s, 56° C. for 30 s, 72° C. for 1 min, and finally 72° C. for 10 min. Amplified products were size fractionated on 1% w/v agarose gel in TAE buffer. Gel electrophoresis was carried out at 80 volts for 40 min before DNA bands were visualized with a BioRad QuantiOne UV transilluminator and software.

Figure 7:
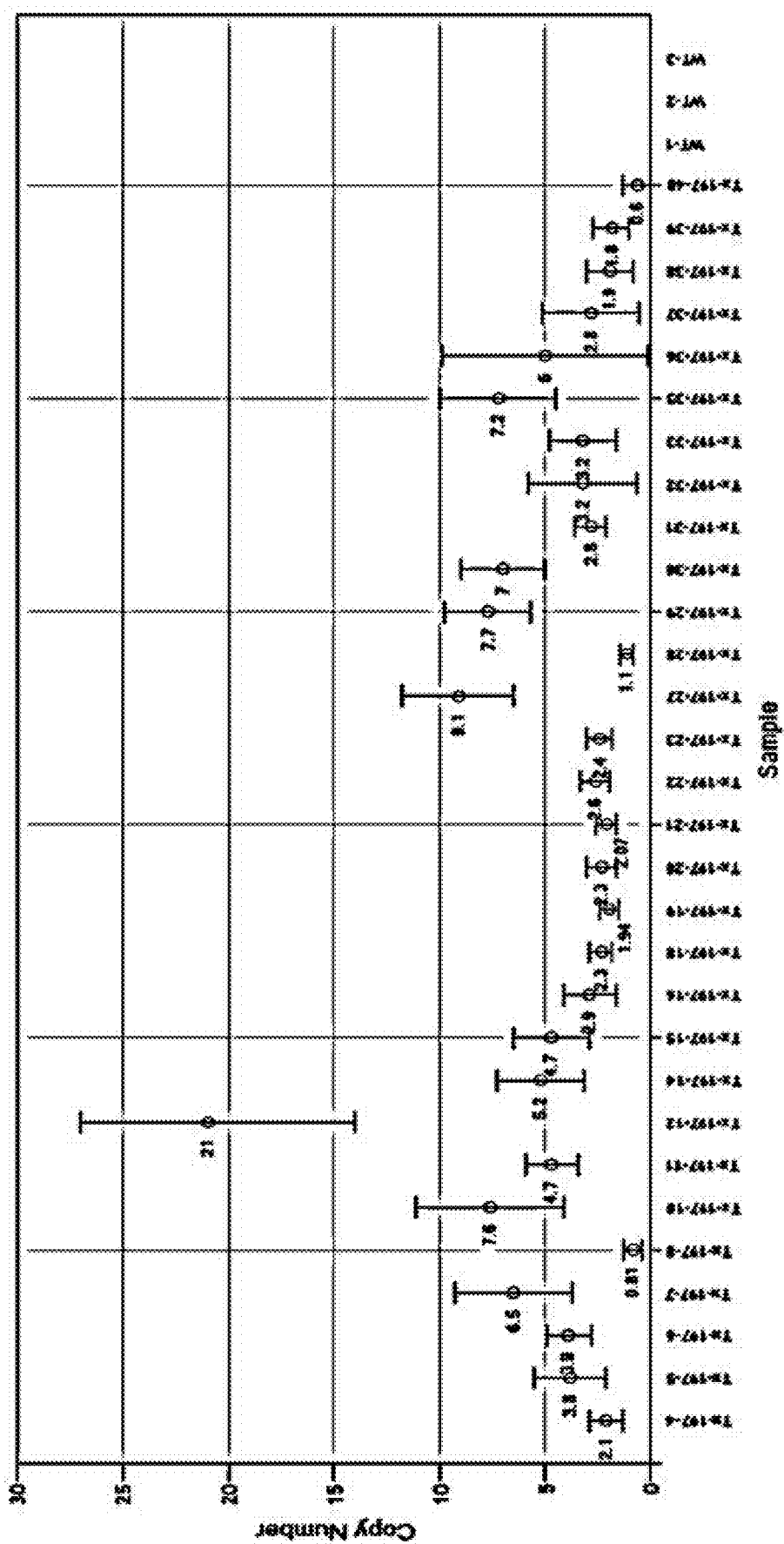
FIG. 7. Copy number of the Npt-II gene in 31 independent T0 transgenic plants analysed by digital droplet PCR.

All the putative transformants were positive for NptII transgene and with the expected 750 bp amplicon (FIG. 7) from an internal segment of the gene. In WT DNA no band was detected. The presence of NptII transgene in all the putative transformants indicated the geneticin selection was suitable and effective for DEC tissues.

Transgene copy number was then analysed by ddPCR using two primer sets, one designed target NptII(transgene) and the other to target an endogenous reference gene ENOL-2 (Xue et al., 2014) which was present in sorghum as two copies. Transgene copy number was determined by Digital Droplet PCR (Katarzyna et al., 2016) using primer and probes described in Table 10 specific for the NptII selectable marker and Sorghum ENOL-2 reference gene (Xue et al., 2014). BamH1 and EcoRI digested genomic DNA was added to ddPCR mastermix at concentrations between 20 ng and 120 ng of DNA per 25 µl PCR reaction. Final concentrations of Sigma primers and IDT probes in the reaction were 400 nM and 200 nM, respectively. Droplets were generated using a Droplet Generator QX200 (Bio-Rad, Australia) following the manufacturer's instructions. 40 µl of droplets in oil emulsion was transferred to a 96-well plate and loaded in a C1000 Thermal Cycler (Bio-Rad, Australia). The PCR thermocycle program consisted of 95° C. for 10 min, 40 cycles of 94° C. for 30 see and 59° C. for 1 min, followed by 98° C. for 10 min, with a 2.5° C./s ramping at each step. After amplification, plates were loaded on to the QX100 Droplet Reader (Bio-Rad, Australia) for the detection of amplicons in individual droplets. Data analysis was performed using the Quanta soft software (version 1.7.4.0917; Bio-Rad, Australia).

Figure 5:
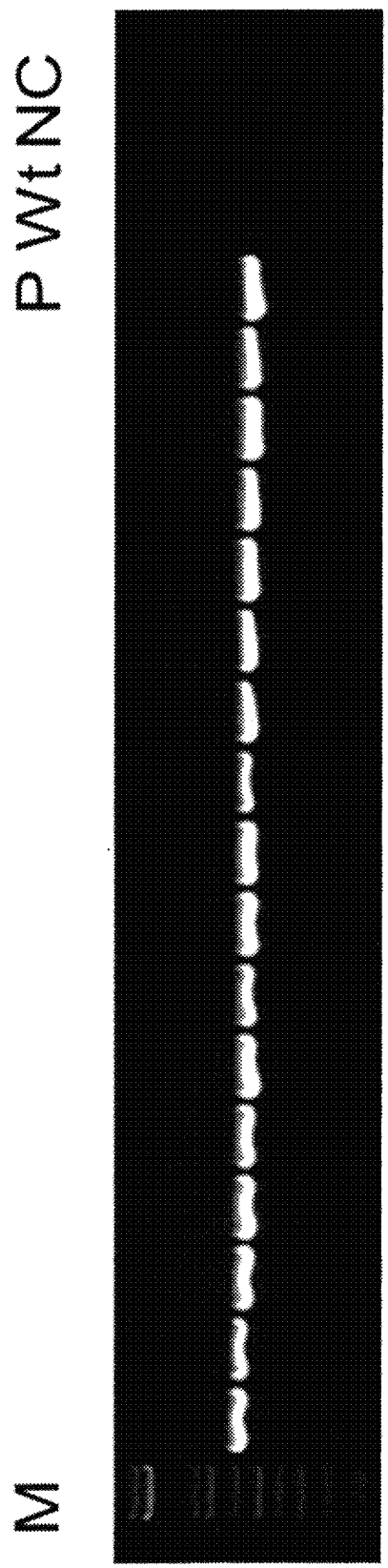
FIG. 5. PCR detection of NptII transgene in randomly selected lines. Lanes from left to right: "M"=1 kb plus DNA ladder; lanes 2-18=transgenic lines, "P"=plasmid DNA; "WT"=WT TX430 DNA; and "NC"=water control.

Variation in copy number of transgene was determined by calculating the concentration of reference and transgene in randomly selected 31 independent T0 events. Eight of 31 transgenic events displayed <2 copies (22.5%), while around 26% of events showed 2-3 copies per diploid genome. The remaining transgenic events (48.3%) were predicted to contain more than 3 copies per diploid genome (FIG. 5).

The inventors concluded that the transformation method using DEC tissues provided an efficient, relatively rapid method that yielded morphologically normal, fertile sorghum plants with no detected non-transgenic plants in the regenerated plant population. The transgenes are inherited in progeny plants, demonstrating that the transgenes are integrated into the sorghum genome.

Example 10—*Agrobacterium*-Mediated Transformation of Green Regenerative DEC Tissues Uniform healthy, green regenerative DEC tissues (4-5 mm in size) produced using methods described in the foregoing examples and which have been cultured for 6 weeks to 6 months from initiation, are used for *Agrobacterium*-mediated transformation.

A genetic vector is obtained for transformation of green regenerative DEC tissues using *Agrobacterium*-mediated transformation. The genetic vector contains uidA (GUS) and bar genes designed for expression in plant cells. The uidA gene is under the regulatory control of a maize polyubiquitin promoter (pUbi) and an *Agrobacterium tumefaciens* octopine synthase polyadenylation/terminator (ocs 3') sequence. The sequence between the promoter and the protein coding region includes the 5' UTR and first intron of the Ubi gene. The uidA reporter gene also contains, within its protein coding region, an intron from a castor bean catalase gene which prevented translation of functional GUS protein in *Agrobacterium*, thereby reducing the background GUS gene expression in inoculated plant tissues. Therefore, any GUS expression would be due to expression of the uidA gene in the plant cells. The bar gene is also under the regulatory control of a pUbi promoter and terminated with an *Agrobacterium* nopaline synthase 3' regulatory sequence (nos 3').

A suitable *Agrobacterium tumefaciens* strain is obtained e.g., AGL1 as described in Lazo et al. (1991) and the genetic vector is introduced into the *Agrobacterium tumefaciens* strain by heat shock method.

*Agrobacterium* cultures harboring the genetic construct are grown in suitable medium e.g., LB medium, and under appropriate conditions to produce an *Agrobacterium* inoculum, after which time the uniform healthy, green regenerative DEC tissues are infected with *Agrobacterium* inoculum. The infected DEC tissues are blotted on sterile filter paper to remove excess *Agrobacterium* and transferred to co-cultivation medium, optionally supplemented with antioxidants, and incubated in the dark at approximately 22-24° C. for 2-4 days. Following incubation, the DEC tissues are treated with

TABLE 10

Primers and probes used in copy number detection

| Gene ID | Forward (5'-3') | Reverse (5'-3') | Probe sequence (5'-3') |
|---|---|---|---|
| NPTII | TACGCTTGATCCGGCTAC (SEQ ID NO: 3) | CTTCCATCCGAGTACGTG (SEQ ID NO: 4) | GAAACATCGCATCGAGCG (SEQ ID NO: 5) |
| ENOL-2 | TGAGGACCCTTTTGATCAGG (SEQ ID NO: 6) | CAAGCCTTCTTGCCAATAGC (SEQ ID NO: 7) | TGGAGTTCATGGGCATCATTGCA (SEQ ID NO: 8) | an appropriate agent to kill the *Agrobacterium*, washed in sterile water, transferred to an appropriate medium and allowed to grow. After 4-6 weeks, shoots are excised and cultured on shoot elongation medium, after which time putative transgenic shoots are then detected using appropriate assays.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Able et al. (2001). *In Vitro Cell Dev Biol Plant* 37:341-348.
Casas et al. (1993). *Proc. Natl. Acad. Sci. USA* 90:11212-11216.
Capecchi (1980) *Cell* 22:479-488.
Chae et al., (2013) *GCB Bioenergy* 5:338-350.
Cho et al. (1998). *Plant Sci* 138:229-244.
Cho et al. (1999). In: Application of Transformation Technology in Plant Breeding. Suwon, Korea, pp 39-53.
Clapp (1993) *Clin. Perinatol.* 20:155-168.
Cong et al. (2013) *Science* 339:819-823.
Curiel et al. (1992) *Hum. Gen. Ther.* 3:147-154.
Day et al. (2004) *Luminescence* 19:8-20.
de Wet et al. (1987) *Mol. Cell. Biol.* 2987:725-737.
Eglitis et al. (1988) *Biotechniques* 6:608-614.
Gelvin et al., Plant Molecular Biology Manual, Kluwer Academic Publishers, 1990.
Greer and Szalay (2002) *Luminescence* 17:43-74.
Groenen et al. (1993) *Mol. Microbiol.* 10:1057-1065.
Grootboom et al. (2010). *Int J Bot* 6:1811-9719.
Gurel et al. (2009) *Plant Cell Rep.* 28(3):429-444.
Haft et al. (2005) *Computational Biology* 1(6):e60
Hastings et al. (2001) *Proc. Natl. Acad. Sci. U.S.A.* 98:14304-14309.
Hinchee et al. (1988) *Biotechnology* 6:915-922.
Hoe et al. (1999) *Emerg. Infect. Dis.* 5:254-263.
Howe et al. (2006). *Plant Cell Rep* 25:784-791.
Hushpulian et al. (2007) *Biotransformation* 25:2-4.
Inouye et al. (1997) *Biochem. J.* 233:349-353.
Ishino et al. (1987) *J. Bacteriol.* 169:5429-5433.
Janssen et al. (2002) *OMICS J. Integ. Biol.* 6:23-33.
Katarzyna et al. (2016) *Plant Cell and Environment* 39:908-917.
Klee et al., In: Plant DNA Infectious Agents, Hohn and Schell, eds., Springer-Verlag, New York, pp. 179-203 (1985).
Li et al. (2016). *Inter. J. Agric. Biol.* doi: 10.17957/IJAB/15.0075.
Liu and Godwin (2012). *Plant Cell Reports* 31, 999-1007.
Liu et al. (2015). *South African Journal of Botany* 98, 157-160.
Loening et al. (2006) *Protein Eng Design Selection* 19:391-400.
Lu et al. (1993) *J. Exp. Med.* 178: 2089-2096.
Maheswari et al. (2010). *Biol Plantarum* 54:647-652.
Masepohl et al. (1996) *Biochim. Biophys. Acta* 1307:26-30.
Mieog et al. (2013) *BMC Plant Biol.* 13:71-79.
Miller (1984). *Crop Sci* 24:1224-1224.
Mojica et al. (1995) *Mol. Microbiol.* 17:85-93.
Mojica et al. (2000) *Mol. Microbiol.* 36:244-246.
Murashige and Skoog (1962). *Physiol. Plant* 15:473-497.
Nishizawa et al. (2003) *Plant J.* 34:647-659.
Nishizawa et al. (2003) *Plant Journal* 34:647-659.
Nakata et al. (1989) *J. Bacteriol.* 171:3553-3556.
Pouwels et al., Cloning Vectors: A Laboratory Manual, 1985, supp. 1987.
Richardson et al. (2014) *Plant Cell Tiss. Org. Cult.* 119: 647-659.
Shridhar et al. (2010). *J. SAT Agric. Res* 8: 1-5.
Stalker et al. (1998) *J. Biol. Chem.* 263:6310-6314.
Tadesse et al. (2003). *Plant Cell Tissue Organ Cult* 75:1-18.
Thillet et al. (1988) *J. Biol. Chem* 263:12500-12508.
van Embden et al. (2000) *J. Bacteriol.* 182:2393-2401.
Venkatesh et al. (2015). Genetic Engineering for Novel Traits. R. Madhusudhana et al (eds.), *Sorghum Molecular Breeding.* 217-226.
Visarada and Sai Kishore (2015). Advances in Genetic Transformation. R. Madhusudhana et al. (eds.), *Sorghum Molecular Breeding.* 199-217.
Vivianii (2002) *Cell. Mol. Life Sci.* 59:1833-1850.
Wagner et al. (1992) *Proc. Natl. Acad. Sci. USA* 89:6099-6103.
Weissbach and Weissbach, Methods for Plant Molecular Biology, Academic Press, 1989.
Weissbach et al., In: Methods for Plant Molecular Biology, Academic Press, San Diego, Calif., (1988).
Wu et al. (2014). *In Vitro Cell. Dev. Biol. Plant,* 50:9-18.
Xue et al. (2014) *Int. J. Mol. Sci.* 15:8846-8862.
Yang et al., Particle Bombardment Technology for Gene Transfer, Oxford Press, Oxford, England (1994).
Zhao et al. (2000). *Plant Mol Biol* 44:789-798.

The invention claimed is:

1. A method for producing genetically modified differentiating embryogenic callus (DEC) tissue of sorghum, the method comprising: (1) preparing differentiating embryogenic callus (DEC) tissue of sorghum, comprising culturing isolated immature embryos (IEs) from sorghum in callus inducing medium (CIM) for a time and under conditions sufficient to produce DEC tissue from the IEs, wherein the CIM comprises a basal medium suitable for culturing plant cells supplemented with one or more auxins, one or more cytokinins and one or more agents which reduces oxidative browning, wherein the one or more agents which reduce oxidative browning comprise lipoic acid at a concentration of 0.5 mg/L to 2.0 mg/L, and (2) introducing one or more nucleic acids into the DEC tissue of sorghum to produce a genetically modified sorghum DEC tissue.

2. The method according to claim 1, wherein the CIM has one or more or all of the following features:
   (i) the one or more auxins are selected from the group consisting of indole-3-acetic acid (IAA), 4-chloroindole-3-acetic acid, phenylacetic acid, indole-3-butyric acid (IBA), 1-naphthaleneacetic acid (NAA), 2-naphthoxyacetic acid, 4-chlorophenoxyacetic acid, 2,4-dichlorophenoxyacetic acid (2,4-D), 2,4,5-trichlorophenoxyacetic acid, 2,3,5-triiodobenzoic acid, picloram, and salt forms of any one thereof;
   (ii) the one or more auxins are present in the CIM at a concentration of 0.1 mg/L to 5 mg/L;
   (iii) the one or more cytokinins are selected from the group consisting of benzylaminopurine (BAP), zeatin, kinetin, 2IP, zeatin riboside, diphenylurea and thidiazuron (TDZ);
   (iv) the one or more cytokinins are present in the CIM at a concentration of 0.01 mg/L to 2 mg/L;
   (v) the one or more auxins and the one or more cytokinins are present in the CIM in amounts relative to one another which is sufficient to produce and/or maintain the DECs from the IEs; and
   (vi) the one or more auxins and the one or more cytokinins are present in the CIM at a weight ratio (auxin:cytokinin) of 2:1.

3. The method according to claim 1, wherein the CIM further comprises one or more or all of the following:
   (i) peptone at a concentration of 0.2 g/L to 2 g/L;
   (ii) copper in the form of cupric sulfate, copper chloride, copper nitrate, copper gluconate, or copper acetate;
   (iii) wherein when copper is present, the copper is present at a concentration of 0.1 mg/L to 5 mg/L; and/or
   (iv) an osmotic agent.

4. A method of producing a genetically-modified sorghum plant or regenerative part thereof, said method comprising in order:
   (a) performing the method of claim 1 on one or more DEC tissues;
   (b) culturing the DEC tissue(s) into which the one or more nucleic acids have been introduced on a medium, or a series of media, such that said culturing induces shoot formation from the DEC tissue(s), thereby producing one or more genetically modified shoot;
   (c) producing one or more genetically modified sorghum plants from the genetically modified shoot of step (b), thereby producing the genetically-modified sorghum plant(s); and optionally
   (d) obtaining regenerative parts from the genetically modified plant(s) of step (c).

5. The method of claim 4, further comprising selfing or crossing the genetically modified sorghum plant with another sorghum plant to produce progeny plants.

6. The method according to claim 5, further comprising:
   (i) screening the progeny plants for the presence of the genetic modification or a phenotype conferred by the genetic modification; and
   (ii) selecting progeny plants comprising the genetic modification and/or which display a phenotype conferred by the genetic modification, to thereby produce the one or more genetically modified sorghum plant(s).

7. The method of claim 1, further comprising a step of splitting the genetically modified sorghum DEC tissue into two or more parts after introduction of the one or more nucleic acids and prior to shoot buds emerging from the genetically modified sorghum DEC tissue.

\* \* \* \* \*

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial sequence
<220> FEATURE:
<223> OTHER INFORMATION: NPTII-F primer

<400> SEQUENCE: 1
```
atgattgaac aagatggatt g                                          21

<210> SEQ ID NO 2
<211> LENGTH: 21
<212> TYPE: DNA
<213> ORGANISM: Artificial sequence
<220> FEATURE:
<223> OTHER INFORMATION: NPTII-R primer

<400> SEQUENCE: 2
gctatgtcct gatagcggtc c                                          21

<210> SEQ ID NO 3
<211> LENGTH: 18
<212> TYPE: DNA
<213> ORGANISM: Artificial sequence
<220> FEATURE:
<223> OTHER INFORMATION: NPTII forward primer

<400> SEQUENCE: 3
tacgcttgat ccggctac                                              18

<210> SEQ ID NO 4
<211> LENGTH: 18
<212> TYPE: DNA
<213> ORGANISM: Artificial sequence
<220> FEATURE:
<223> OTHER INFORMATION: NPTII reverse primer

<400> SEQUENCE: 4
cttccatccg agtacgtg                                              18

<210> SEQ ID NO 5
<211> LENGTH: 18
<212> TYPE: DNA
<213> ORGANISM: Artificial sequence
<220> FEATURE:
<223> OTHER INFORMATION: NPTII probe sequence

<400> SEQUENCE: 5
gaaacatcgc atcgagcg                                              18

<210> SEQ ID NO 6
<211> LENGTH: 20
<212> TYPE: DNA
<213> ORGANISM: Artificial sequence
<220> FEATURE:
<223> OTHER INFORMATION: ENOL-2 forward primer

<400> SEQUENCE: 6
tgaggaccct tttgatcagg                                            20

<210> SEQ ID NO 7
<211> LENGTH: 20
<212> TYPE: DNA
<213> ORGANISM: Artificial sequence
<220> FEATURE:
<223> OTHER INFORMATION: ENOL-2 reverse primer

<400> SEQUENCE: 7
caagccttct tgccaatagc                                            20

<210> SEQ ID NO 8
<211> LENGTH: 23
<212> TYPE: DNA
<213> ORGANISM: Artificial sequence

```
<220> FEATURE:
<223> OTHER INFORMATION: ENOL-2 probe sequence

<400> SEQUENCE: 8
tggagttcat gggcatcatt gca                                                23
```